United States Patent
Jang

(10) Patent No.: US 12,195,467 B2
(45) Date of Patent: Jan. 14, 2025

(54) COMPOUND HAVING TrkA INHIBITORY ACTIVITY AND PHARMACEUTICAL COMPOSITION, FOR PREVENTING OR ALLEVIATING PAIN, CONTAINING SAME AS ACTIVE INGREDIENT

(71) Applicant: JBKLAB CO., LTD., Gyeonggi-do (KR)

(72) Inventor: Bong Keun Jang, Gyeonggi-do (KR)

(73) Assignee: JBKLAB Co., Ltd., Gyeonggi-do (KR)

( * ) Notice: Subject to any disclaimer, the term of this patent is extended or adjusted under 35 U.S.C. 154(b) by 944 days.

(21) Appl. No.: 17/261,944

(22) PCT Filed: Jun. 3, 2019

(86) PCT No.: PCT/KR2019/006648
§ 371 (c)(1),
(2) Date: Jan. 21, 2021

(87) PCT Pub. No.: WO2020/022636
PCT Pub. Date: Jan. 30, 2020

(65) Prior Publication Data
US 2021/0309665 A1    Oct. 7, 2021

(30) Foreign Application Priority Data
Jul. 26, 2018  (KR) .................. 10-2018-0087092

(51) Int. Cl.
| | | |
|---|---|---|
| *C07D 487/04* | (2006.01) | |
| *A23L 33/10* | (2016.01) | |
| *A61K 9/00* | (2006.01) | |
| *A61K 9/08* | (2006.01) | |
| *A61K 9/16* | (2006.01) | |
| *A61K 9/20* | (2006.01) | |
| *A61K 9/48* | (2006.01) | |
| *A61K 47/26* | (2006.01) | |
| *C07D 471/04* | (2006.01) | |

(52) U.S. Cl.
CPC ............ *C07D 487/04* (2013.01); *A23L 33/10* (2016.08); *C07D 471/04* (2013.01); *A61K 9/0019* (2013.01); *A61K 9/0053* (2013.01); *A61K 9/08* (2013.01); *A61K 9/1611* (2013.01); *A61K 9/1623* (2013.01); *A61K 9/2018* (2013.01); *A61K 9/2059* (2013.01); *A61K 9/4858* (2013.01); *A61K 47/26* (2013.01)

(58) Field of Classification Search
CPC .................. C07D 487/04; C07D 471/104
See application file for complete search history.

(56) References Cited

U.S. PATENT DOCUMENTS

2008/0194557 A1   8/2008   Barbosa et al. ........... 514/234.5

FOREIGN PATENT DOCUMENTS

| KR | 101753654 | 5/2017 |
|---|---|---|
| KR | 1020170046847 | 5/2017 |
| KR | 1020130066621 | 11/2017 |
| KR | 1020150038295 | 6/2020 |
| WO | 2008/112695 A2 | 9/2008 |
| WO | 2008/112695 A3 | 10/2008 |
| WO | 2012/135631 | 10/2012 |
| WO | 2013/085802 | 6/2013 |
| WO | 2015/143652 A1 | 10/2015 |
| WO | 2015/143652 A8 | 10/2015 |
| WO | 2015/143653 A1 | 10/2015 |

OTHER PUBLICATIONS

Registry No. 2096371-48-9, File Registry on STN, entered STN May 19, 2017.*
Abdelazeem et al. "Novel pyrazolopyrimidine derivatives targeting COXs and iNOS enzymes; design, synthesis and biological evaluation as potential anti-inflammatory agent" European Journal of Pharmaceutical Sciences 2014 62:197-211.
Patapoutian, A & Reichardt, L.F. "Trk receptors : mediators of neurotropin action" Current Opinion in Neurobiology 2001 11:272-280.

* cited by examiner

*Primary Examiner* — Rebecca L Anderson
(74) *Attorney, Agent, or Firm* — Licata & Tyrrell P.C.

(57) ABSTRACT

The present invention relates to a compound having TrkA inhibitory activity and a pharmaceutical composition for preventing or treating pain containing the same as an active ingredient. The compound provided in one aspect of the present invention has excellent TrkA inhibitory activity and exhibits excellent pain inhibitory effects in an animal model of pain after a surgery, and thus can be effectively used as an analgesic.

7 Claims, 10 Drawing Sheets

[Figure 1]
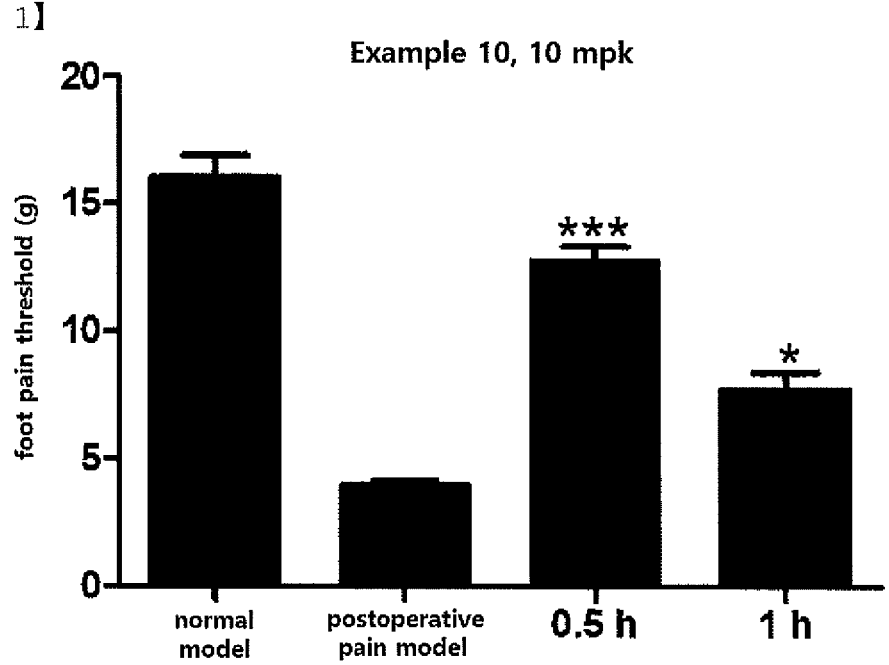

[Figure 2]
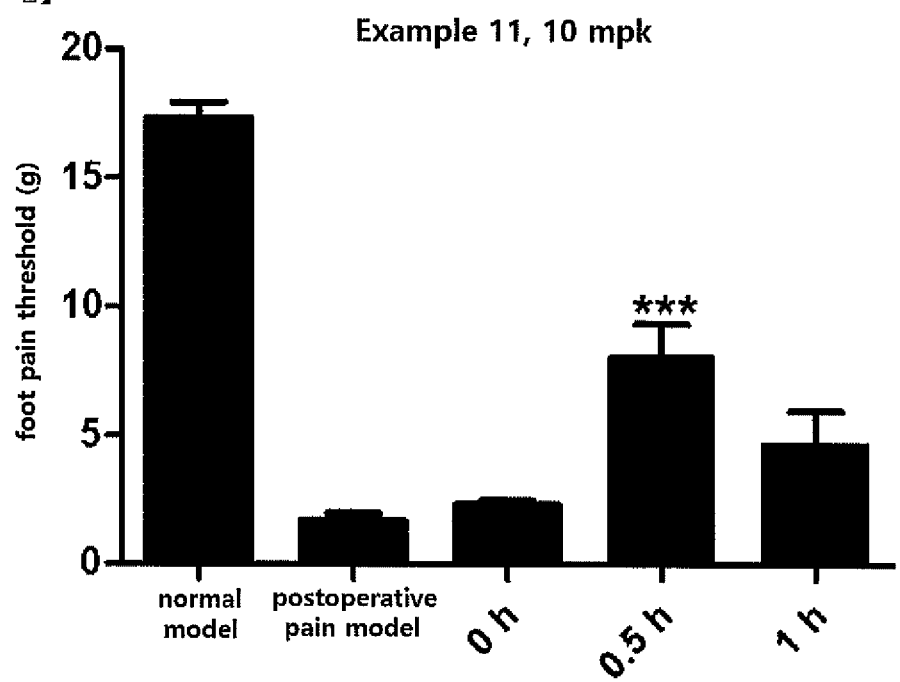

[Figure 3]
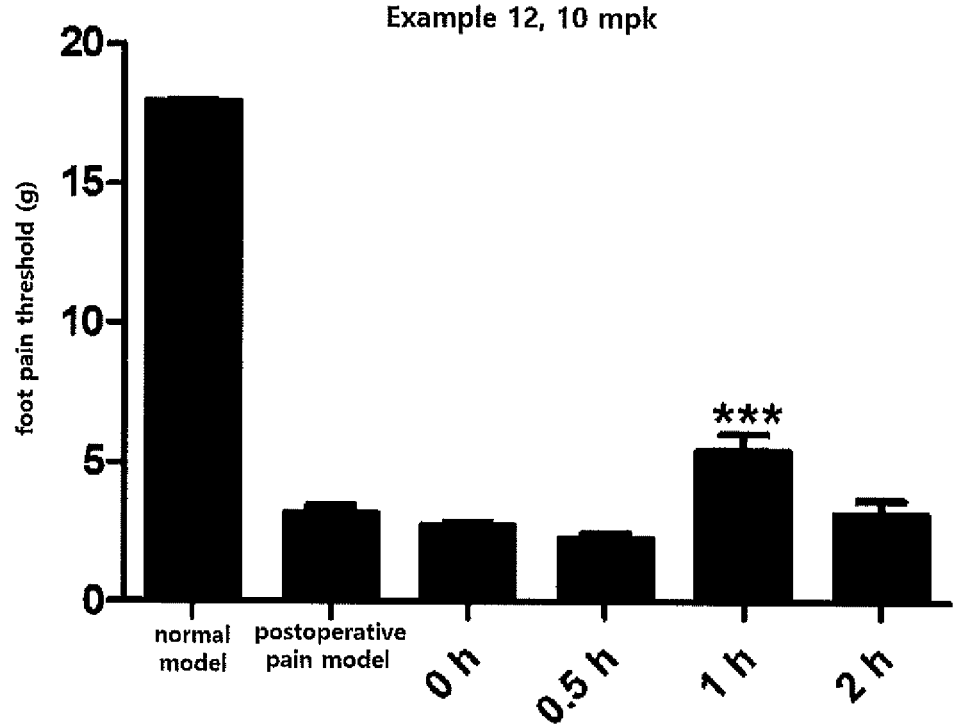

[Figure 4]
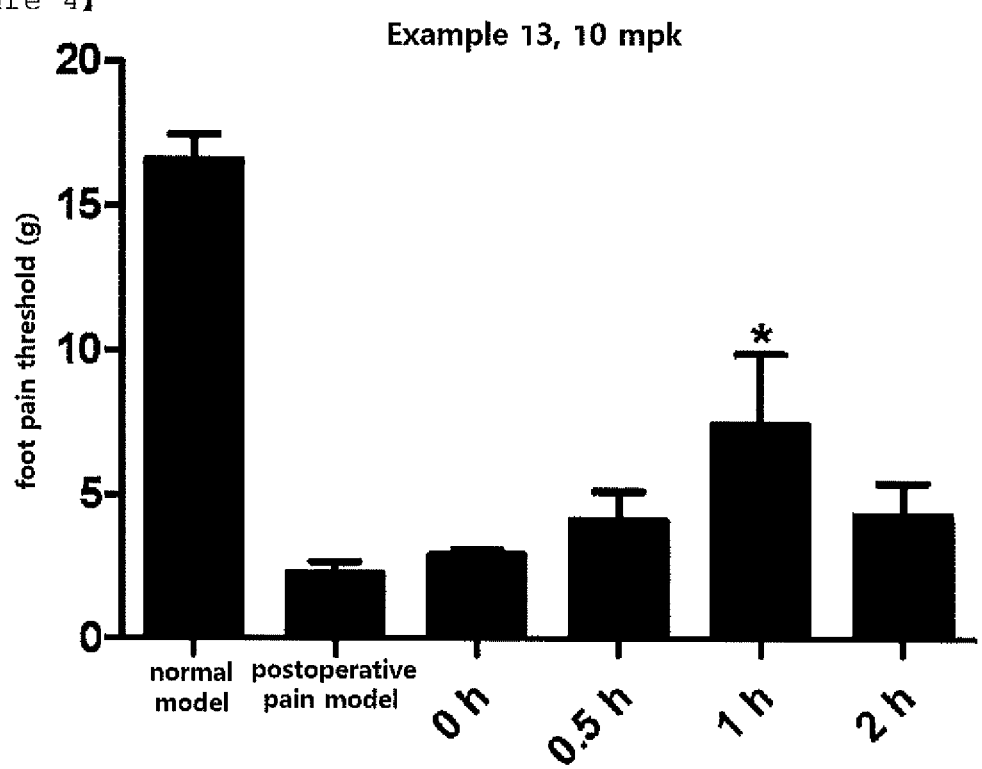

[Figure 5]
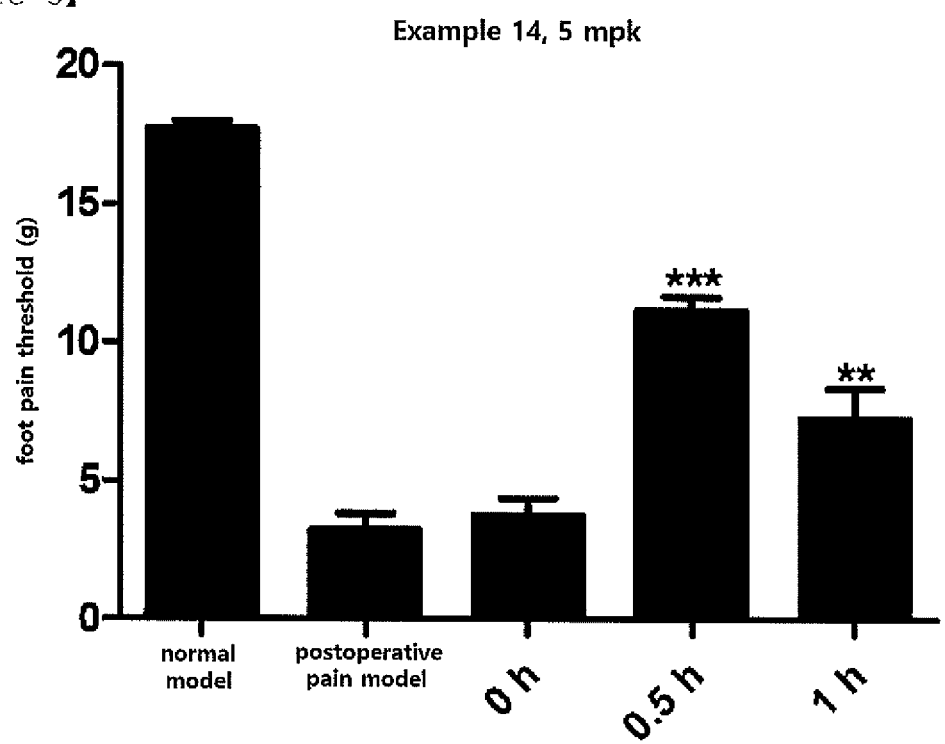

[Figure 6]
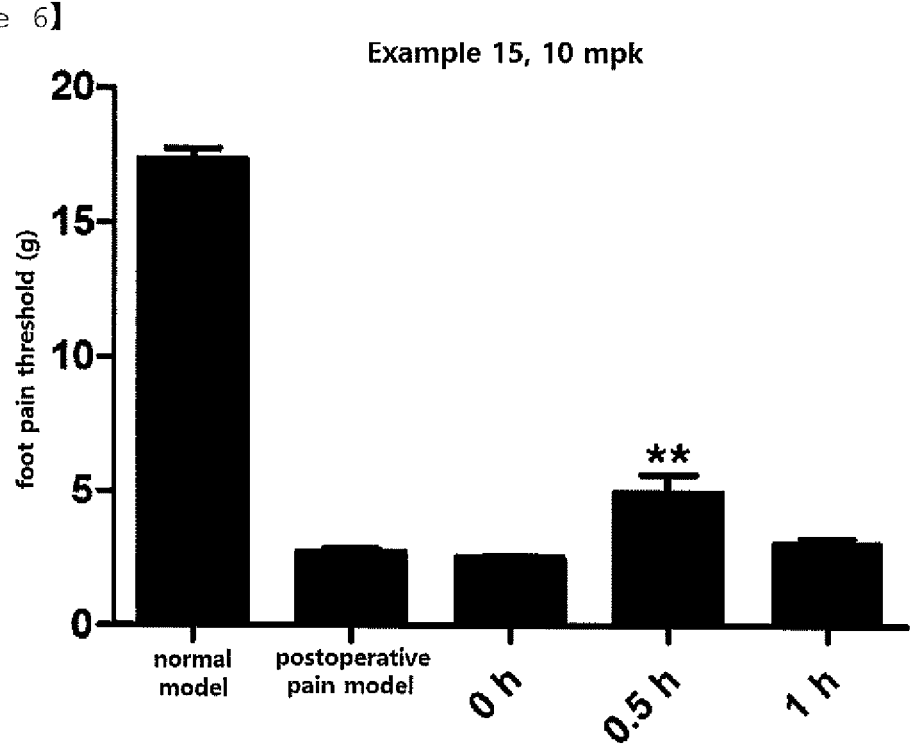

[Figure 7]
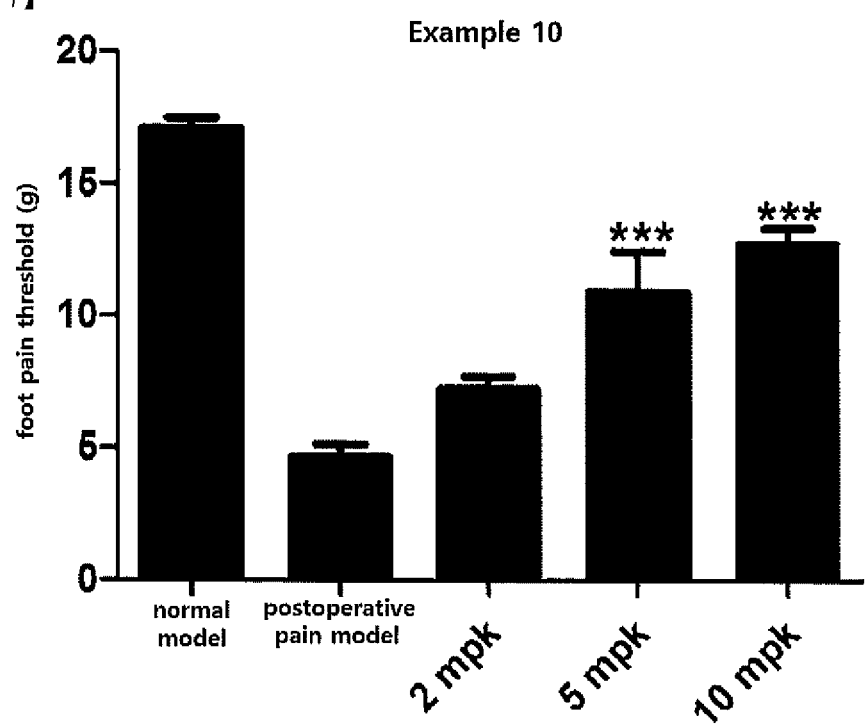

[Figure 8]
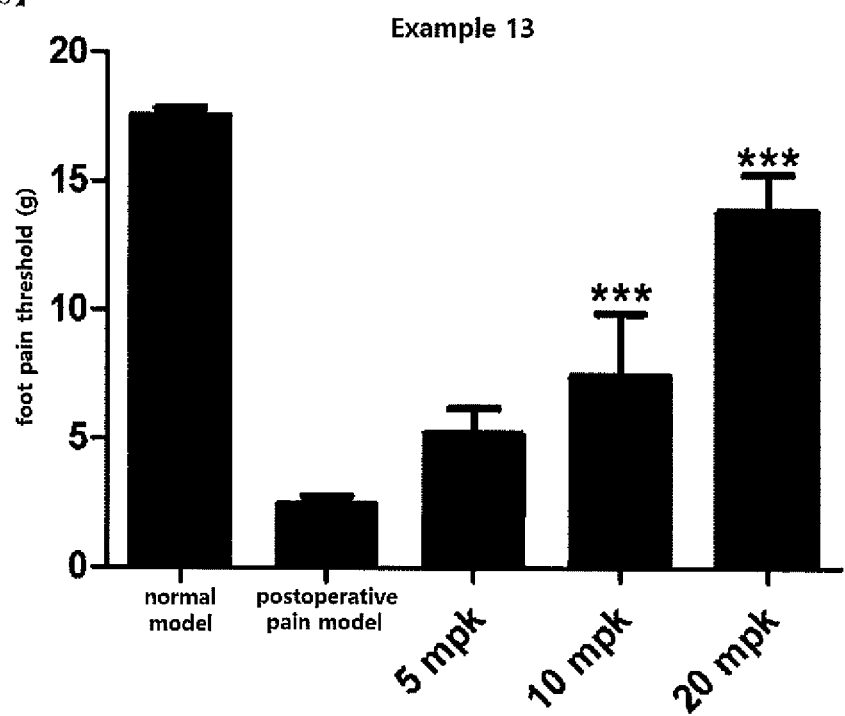

[Figure 9]
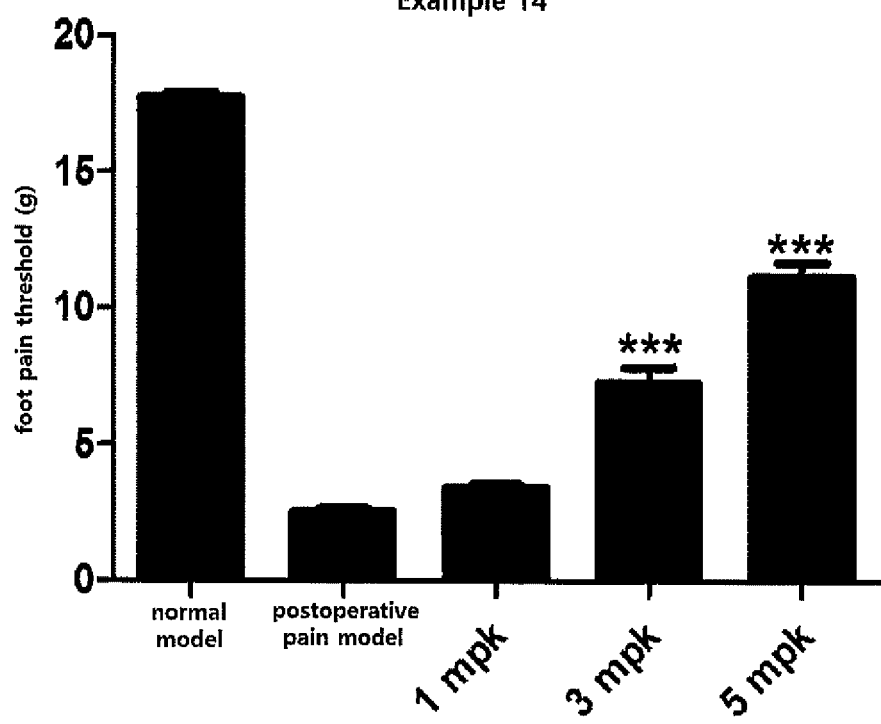

[Figure 10]
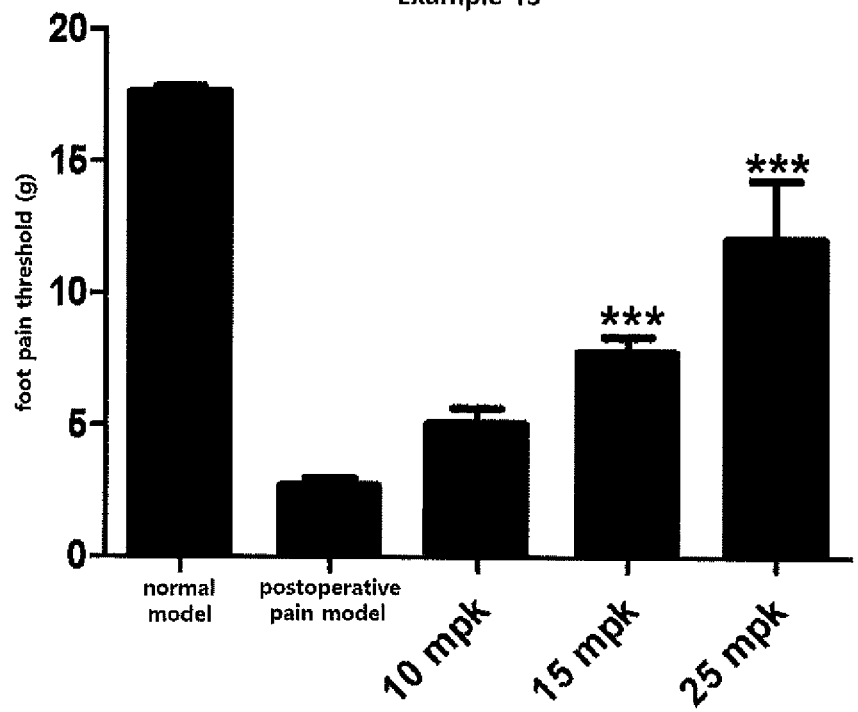

COMPOUND HAVING TrkA INHIBITORY ACTIVITY AND PHARMACEUTICAL COMPOSITION, FOR PREVENTING OR ALLEVIATING PAIN, CONTAINING SAME AS ACTIVE INGREDIENT

This patent application is the U.S. National Stage of PCT/KR2019/006648 filed Jun. 3, 2019, which claims the benefit of priority from Korean Patent Application No. 10-2018-0087092, filed on Jul. 26, 2018 the content of each of which is incorporated herein by reference.

BACKGROUND OF THE INVENTION

1. Field of the Invention

The present invention relates to a compound having TrkA inhibitory activity and a pharmaceutical composition for preventing or treating pain containing the same as an active ingredient.

2. Description of the Related Art

Current therapies for the treatment of pain use several classes of compounds. Opioids (such as morphine) have several disadvantages, including vomiting, constipation and negative respiratory effects, as well as addiction potential. Non-steroidal anti-inflammatory drugs (NSAID, such as COX-1 or COX-2 type) also have disadvantages including insufficient efficacy for treating severe pain. In addition, COX-1 inhibitors can cause mucosal ulcers. Therefore, there is a continuing need for novel and more effective treatments for relief of pain, especially chronic pain.

Trk is a high affinity receptor tyrosine kinase activated by a soluble growth factor group called neurotropin (NT). The Trk receptor family has three members: TrkA, TrkB and TrkC. Among the neurotropins, there are nerve growth factor (NGF) that activates TrkA (i), brain-derived neuroaffinity factor (BDNF) and NT-4/5 that activate TrkB (ii), and NT3 that activates TrkC (iii). Trk is widely expressed in nerve tissues and is involved in the maintenance, signaling and survival of nerve cells (non-patent reference 1, Patapoutian, A. et al., Current Opinion in Neurobiology, 2001, 11, 272-280). Inhibitors of Trk/neurotropin pathway have proven to be effective in a number of preclinical animal models of pain.

In addition, NGF secreted by macrophages invading tumor cells and tumors has been shown to directly stimulate TrkA located in peripheral pain fibers. Neutralization of NGF with monoclonal antibodies has been proved to suppress cancer-related pain to a similar or superior degree to that of administration of the highest tolerated dose of morphine in a variety of mouse and rat tumor models. Because TrkA kinase can act as a mediator of NGF-driven biological responses, inhibitors of TrkA and/or other Trk kinases can provide an effective treatment for chronic pain conditions.

SUMMARY OF THE INVENTION

It is an object of the present invention to provide a compound having excellent TrkA inhibitory activity.

It is another object of the present invention to provide a pharmaceutical composition for preventing or treating pain containing the above compound as an active ingredient.

It is another object of the present invention to provide a health functional food composition for preventing or ameliorating pain containing the above compound as an active ingredient.

It is another object of the present invention to provide a method for treating pain comprising a step of administering the above compound to a subject in need thereof.

It is another object of the present invention to provide the above compound for use in the prevention or treatment of pain.

It is another object of the present invention to provide a use of the above compound for preparing a medicament for use in the prevention or treatment of pain.

To achieve the above objects, in one aspect of the present invention, the present invention provides a compound represented by formula 1, a stereoisomer thereof or a pharmaceutically acceptable salt thereof.

In another aspect of the present invention, the present invention provides a pharmaceutical composition for preventing or treating pain containing the above compound as an active ingredient.

In another aspect of the present invention, the present invention provides a health functional food composition for preventing or ameliorating pain containing the above compound as an active ingredient.

In another aspect of the present invention, the present invention provides a method for treating pain comprising a step of administering the above compound to a subject in need thereof.

In another aspect of the present invention, the present invention provides the above compound for use in the prevention or treatment of pain.

In another aspect of the present invention, the present invention provides a use of the above compound for preparing a medicament for use in the prevention or treatment of pain.

Advantageous Effect

The compound provided in one aspect of the present invention has excellent TrkA inhibitory activity and exhibits excellent pain inhibitory effects in an animal model of pain after a surgery, and thus can be effectively used as an analgesic.

BRIEF DESCRIPTION OF THE DRAWINGS

FIG. 1 is a graph showing the optimal drug expression time of the compound of Example 10 in each postoperative pain animal model.

FIG. 2 is a graph showing the optimal drug expression time of the compound of Example 11 in each postoperative pain animal model.

FIG. 3 is a graph showing the optimal drug expression time of the compound of Example 12 in each postoperative pain animal model.

FIG. 4 is a graph showing the optimal drug expression time of the compound of Example 13 in each postoperative pain animal model.

FIG. 5 is a graph showing the optimal drug expression time of the compound of Example 14 in each postoperative pain animal model.

FIG. 6 is a graph showing the optimal drug expression time of the compound of Example 15 in each postoperative pain animal model.

FIG. 7 is a graph showing the pain suppressing effect of the compound of Example 10 according to the concentration at the optimal drug expression time in each postoperative pain animal model.

FIG. 8 is a graph showing the pain suppressing effect of the compound of Example 13 according to the concentration at the optimal drug expression time in each postoperative pain animal model.

FIG. 9 is a graph showing the pain suppressing effect of the compound of Example 14 according to the concentration at the optimal drug expression time in each postoperative pain animal model.

FIG. 10 is a graph showing the pain suppressing effect of the compound of Example 15 according to the concentration at the optimal drug expression time in each postoperative pain animal model.

DESCRIPTION OF THE PREFERRED EMBODIMENTS

Hereinafter, the present invention is described in detail.

In one aspect of the present invention, the present invention provides a compound represented by formula 1, a stereoisomer thereof or a pharmaceutically acceptable salt thereof.

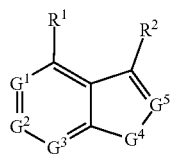

[Formula 1]

In formula 1,

R$^1$ is nonsubstituted or substituted 5-10 membered heteroaryl containing one or more heteroatoms selected from the group consisting of H, N, O and S, nonsubstituted or substituted 6-10 membered heterocycloalkyl containing one or more heteroatoms selected from the group consisting of N, O and S, nonsubstituted or substituted $C_{6-10}$ aryl, or —NHE$^1$, the substituted 5-10 membered heteroaryl, 6-10 membered heterocycloalkyl and $C_{6-10}$ aryl are independently —OH, —F, —Cl, —Br, —I, nonsubstituted or substituted 5-6 membered heterocycloalkyl containing one N, 5-10 membered heteroaryl substituted with one or more substituents selected from the group consisting of aminocarbonyl and aminocarbonylamino, 6-10 membered heterocycloalkyl and $C_{6-10}$ aryl, the substituted 5-6 membered heterocycloalkyl is 5-6 membered heterocycloalkyl substituted with

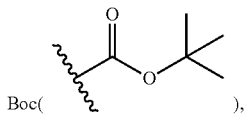

E$^1$ is 5-10 membered cycloalkyl nonsubstituted or substituted with one or more —OH;

R$^2$ is —H, nonsubstituted or substituted $C_{6-10}$ aryl, nonsubstituted or substituted $C_{6-10}$ arylamino, or nonsubstituted or substituted $C_{6-10}$ arylcarbonylamino, the substituted $C_{6-10}$ aryl, $C_{6-10}$ arylamino and $C_{6-10}$ arylcarbonylamino are independently $C_{6-10}$ aryl, $C_{6-10}$ arylamino and $C_{6-10}$ arylcarbonylamino substituted with one or more substituents selected from the group consisting of —OH, —F, —Cl, —Br, —I and nonsubstituted or substituted 6-membered heterocycloalkyl containing two Ns, the substituted 6-membered heterocycloalkyl is 6-membered heterocycloalkyl substituted with $C_{1-5}$ straight or branched alkyl;

G$^1$ is =CA$^1$- or =N—,

A$^1$ is —H, —F, —Cl, —Br, —I, nonsubstituted or substituted $C_{6-10}$ aryl, or nonsubstituted or substituted 5-10 membered heteroaryl containing one or more heteroatoms selected from the group consisting of N, O and S, the substituted $C_{6-10}$ aryl and 5-10 membered heteroaryl are independently $C_{6-10}$ aryl and 5-10 membered heteroaryl substituted with one or more substituents selected from the group consisting of —F, —Cl, —Br, —I, methyl, nitro, $C_{1-5}$ straight or branched alkylaminocarbonylamino and nonsubstituted 6-membered heterocycloalkyl containing one N;

G$^2$ is =CA$^2$- or =N—,

A$^2$ is —H;

G$^3$ is =CA$^3$- or =N—,

A$^3$ is —H;

G$^4$ is —NA$^4$-,

A$^4$ is —H, or nonsubstituted or substituted benzyl, the substituted benzyl is benzyl substituted with $C_{1-5}$ straight or branched alkoxy;

G$^5$ is =CA$^5$- or =N—, and

A$^5$ is —H.

In another aspect,

R$^1$ is —H, nonsubstituted or substituted 5-membered heteroaryl containing two Ns, nonsubstituted or substituted 6-membered heterocycloalkyl containing one N, nonsubstituted or substituted phenyl or —NHE$^1$, the substituted 5-membered heteroaryl, 6-membered heterocycloalkyl and phenyl are independently 5-membered heteroaryl, 6-membered heterocycloalkyl and phenyl substituted with one or more substituents selected from the group consisting of —OH, —F, —Cl, —Br, —I, nonsubstituted or substituted 5-6 membered heterocycloalkyl containing one N, aminocarbonyl and aminocarbonylamino, the substituted 5-6 membered heterocycloalkyl is 5-6 membered heterocycloalkyl substituted with

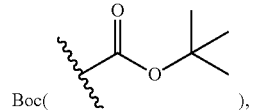

E$^1$ is 5-6 membered cycloalkyl nonsubstituted or substituted with one or more —OH;

R$^2$ is —H, nonsubstituted or substituted phenyl, nonsubstituted or substituted phenylamino, or nonsubstituted or substituted phenylcarbonylamino, the substituted phenyl, phenylamino and phenylcarbonylamino are independently phenyl, phenylamino and phenylcarbonylamino substituted with one or more substituents selected from the group consisting of —OH, —F, —Cl, —Br, —I and nonsubstituted or substituted 6-membered heterocycloalkyl containing two Ns, the substituted 6-membered heterocycloalkyl is 6-membered heterocycloalkyl substituted with methyl;

$G^1$ is =CA$^1$- or =N—, $A^1$ is —F, —Cl, —Br, —I, nonsubstituted or substituted phenyl, or nonsubstituted or substituted 5-6 membered heteroaryl containing one or two Ns, the substituted phenyl and 5-6 membered heteroaryl are independently phenyl and 5-6 membered heteroaryl substituted with one or more substituents selected from the group consisting of —F, —Cl, —Br, I, methyl, $C_{1-5}$ straight or branched alkylaminocarbonylamino and nonsubstituted 6-membered heterocycloalkyl containing one N;

$G^2$ is =CA$^2$- or =N—, $A^2$ is —H;

$G^3$ is =CA$^3$- or =N—, $A^3$ is —H;

$G^4$ is —NA$^4$-, $A^4$ is —H, or nonsubstituted or substituted benzyl, the substituted benzyl is benzyl substituted with $C_{1-5}$ straight or branched alkoxy;

$G^5$ is =CA$^5$- or =N—, and $A^5$ is —H.

In another aspect, $R^3$— is —H,

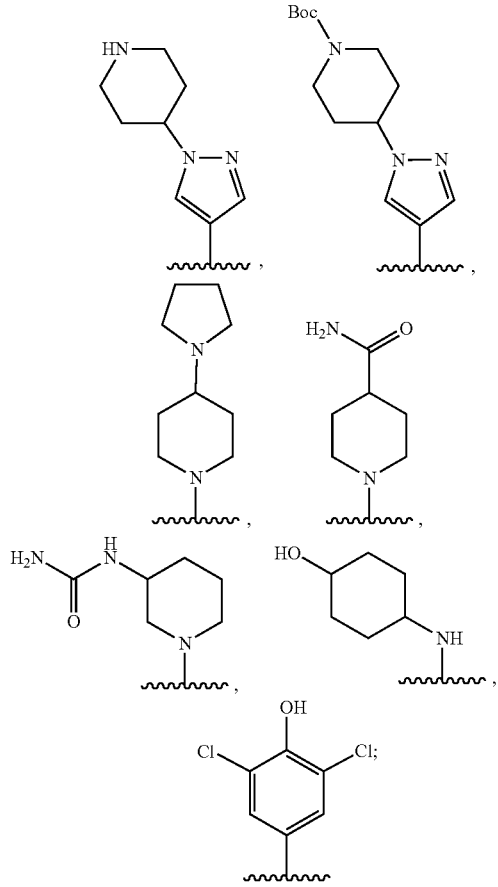

$R^2$ is

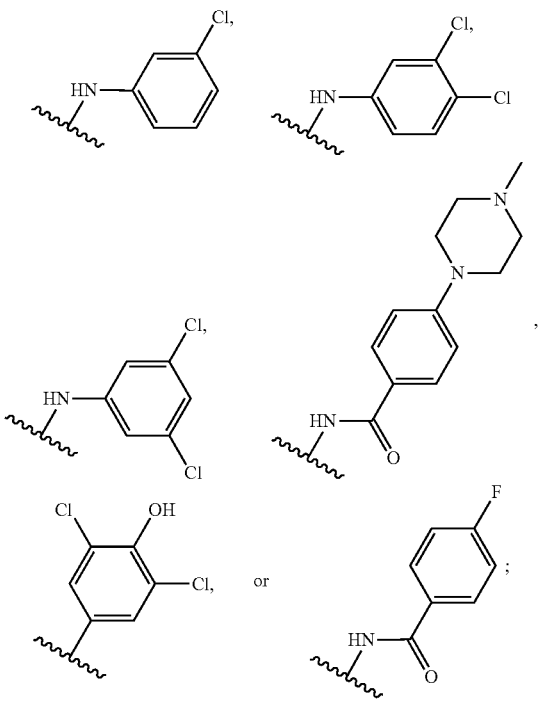

$G^1$ is —CA$^1$- or =N—, $A^1$ is —Br,

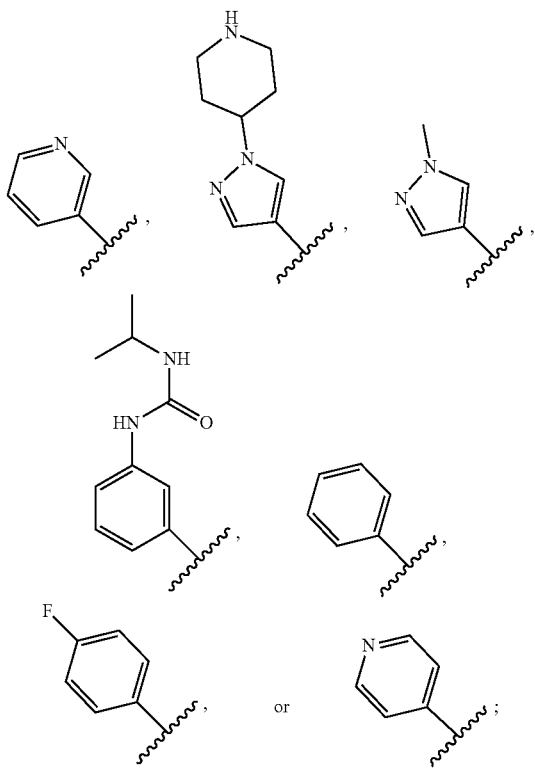

$G^2$ is =CA$^2$- or =N—, $A^2$ is —H;

G³ is =CA³- or =N—,
A³ is —H;
G⁴ is —NA⁴-,
A⁴ is —H, or

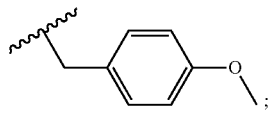

G⁵ is =CA⁵- or =N—,
A⁵ is —H.

The above compound can be any compound selected from the group consisting of the following compounds.

(1) N-(3-chlorophenyl)-5-(pyridine-3-yl)-1H-pyrazolo[3,4-c]pyridine-3-amine;
(2) N-(3,4-dichlorophenyl)-5-(1-(piperidine-4-yl)-1H-pyrazole-4-yl)-1H-pyrazolo[3,4-c]pyridine-3-amine;
(3) N-(3,5-dichlorophenyl)-5-(1-(piperidine-4-yl)-1H-pyrazole-4-yl)-1H-pyrazolo[3,4-c]pyridine-3-amine;
(4) N-(3-chlorophenyl)-5-(1-methyl-1H-pyrazole-4-yl)-1H-pyrazolo[3,4-b]pyridine-3-amine;
(5) N-(3,4-dichlorophenyl)-5-(1-methyl-1H-pyrazole-4-yl)-1H-pyrazolo[3,4-b]pyridine-3-amine;
(6) N-(3,5-dichlorophenyl)-5-(1-methyl-1H-pyrazole-4-yl)-1H-pyrazolo[3,4-b]pyridine-3-amine;
(7) N-(3,5-dichlorophenyl)-5-(1-(piperidine-4-yl)-1H-pyrazole-4-yl)-1H-pyrazolo[3,4-b]pyridine-3-amine;
(8) 4-(4-methylpiperazine-1-yl)-N-(5-(1-(piperidine-4-yl)-1H-pyrazole-4-yl)-1H-pyrazolo[3,4-b]pyridine-3-yl)benzamide;
(9) N-(5-(3-(3-isopropylureido)phenyl)-1H-pyrazolo[3,4-b]pyridine-3-yl)-4-(4-methylpiperazine-1-yl)benzamide;
(10) 4-(4-methylpiperazine-1-yl)-N-(5-phenyl-1H-pyrazolo[3,4-b]pyridine-3-yl)benzamide;
(11) N-(5-(4-fluorophenyl)-1H-pyrazolo[3,4-b]pyridine-3-yl)-4-(4-methylpiperazine-1-yl)benzamide;
(12) 4-(4-methylpiperazine-1-yl)-N-(5-(pyridine-3-yl)-1H-pyrazolo[3,4-b]pyridine-3-yl)benzamide;
(13) 4-(4-methylpiperazine-1-yl)-N-(5-(pyridine-4-yl)-1H-pyrazolo[3,4-b]pyridine-3-yl)benzamide;
(14) N-(5-bromo-1H-pyrazolo[3,4-b]pyridine-3-yl)-4-(4-methylpiperazine-1-yl)benzamide;
(15) 2,6-dichloro-4-(4-(1-(piperidine-4-yl)-1H-pyrazole-4-yl)-7H-pyrrolo[2,3-d]pyrimidine-5-yl)phenol;
(16) N-(7-(4-methoxybenzyl)-4-(1-(piperidine-4-yl)-1H-pyrazole-4-yl)-7H-pyrrolo[2,3-d]pyrimidine-5-yl)-4-(4-methylpiperazine-1-yl)benzamide;
(17) 4-(4-methylpiperazine-1-yl)-N-(4-(1-(piperidine-4-yl)-1H-pyrazole-4-yl)-7H-pyrrolo[2,3-d]pyrimidine-5-yl)benzamide;
(18) tert-butyl 4-(4-(5-(4-(4-methylpiperazine-1-yl)benzamido)-7H-pyrrolo[2,3-d]pyrimidine-4-yl)-1H-pyrazole-1-yl)piperidine-1-carboxylate;
(19) 4-(4-methylpiperazine-1-yl)-N-(4-(4-(pyrrolidine-1-yl)piperidine-1-yl)-7H-pyrrolo[2,3-d]pyrimidine-5-yl)benzamide;
(20) 1-(5-(4-(4-methylpiperazine-1-yl)benzamido)-7H-pyrrolo[2,3-d]pyrimidine-4-yl)piperidine-4-carboxamide;
(21) 4-(4-methylpiperazine-1-yl)-N-(4-(3-ureidopiperidine-1-yl)-7H-pyrrolo[2,3-d]pyrimidine-5-yl)benzamide;
(22) 4-fluoro-N-(5-(1-(piperidine-4-yl)-1H-pyrazole-4-yl)-1H-pyrazolo[3,4-b]pyridine-3-yl)benzamide;
(23) 2,6-dichloro-4-(4-((1s,4s)-4-hydroxycyclohexylamino)-7H-pyrrolo[2,3-d]pyrimidine-5-yl)phenol; and
(24) N-(4-(3,5-dichloro-4-hydroxyphenyl)-7H-pyrrolo[2,3-d]pyrimidine-5-yl)-4-(4-methylpiperazine-1-yl)benzamide.

The compound represented by formula 1 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate.

The acid addition salt according to the present invention can be prepared by the conventional method known to those in the art. For example, the derivative represented by formula 1 is dissolved in an organic solvent such as methanol, ethanol, acetone, dichloromethane, and acetonitrile, to which organic acid or inorganic acid is added to induce precipitation. Then, the precipitate is filtered and dried to give the salt. Or the solvent and the excessive acid are distillated under reduced pressure, and dried to give the salt. Or the precipitate is crystallized in an organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

Furthermore, the present invention includes not only the compound represented by formula 1 and the pharmaceutically acceptable salt thereof, but also solvates, optical isomers, hydrates, etc., which may be prepared therefrom.

In another aspect of the present invention, the present invention provides a pharmaceutical composition for preventing or treating pain containing the above compound, the stereoisomer thereof or the pharmaceutically acceptable salt thereof as an active ingredient. At this time, the compound can be one that inhibits TrkA (Tropomyosin receptor kinase A) to exhibit a preventive or therapeutic activity for pain. The pharmaceutical composition can be an analgesic composition.

The pain described herein includes all types of known pain, such as postoperative pain, pain due to disease, pain due to inflammation, pain due to trauma, acute pain, chronic pain including neuropathic pain, etc.

The disease includes all of the pain associated with any of a number of pathological conditions, such as cancer, fibromyalgia, lower back pain, neck pain, sciatica and osteoarthritis, and the like. The neuropathic pain includes all of the pain caused by the nerves being affected as nerve damage, neuropathy or other diseases progress.

The compound represented by formula 1 or the pharmaceutically acceptable salt thereof can be administered in various oral and parenteral formulations during clinical administration. When the compound represented by formula 1 or the pharmaceutically acceptable salt thereof is formulated, generally used diluents or excipients such as fillers, extenders, binders, wetting agents, disintegrating agents and surfactants are used. Solid formulations for oral administration are tablets, pills, powders, granules and capsules. These solid formulations are prepared by mixing one or more compounds with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions and emulsions. Water insoluble excipients and suspensions can contain, in addition to the active compound or compounds, propylene glycol, polyethylene glycol, vegetable oil like olive oil, injectable ester like ethylolate, etc.

The pharmaceutical composition comprising the compound represented by formula 1 or the pharmaceutically acceptable salt thereof as an active ingredient can be administered by parenterally and the parenteral administration includes subcutaneous injection, intravenous injection, intramuscular injection, or intrathoracic injection.

To prepare the compound represented by formula 1 or the pharmaceutically acceptable salt thereof as a formulation for parenteral administration, the compound represented by formula 1 or the pharmaceutically acceptable salt thereof is mixed with a stabilizer or a buffering agent in water to produce a solution or a suspension, which is then formulated as ampoules or vials. The composition herein can be sterilized and additionally contains preservatives, stabilizers, wettable powders or emulsifiers, salts and/or buffers for the regulation of osmotic pressure, and other therapeutically useful materials, and the composition can be formulated by the conventional mixing, granulating or coating method.

The formulations for oral administration are exemplified by tablets, pills, hard/soft capsules, solutions, suspensions, emulsions, syrups, granules, elixirs, and troches, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatine, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavours, and sweeteners can be additionally included thereto.

In another aspect of the present invention, the present invention provides a health functional food composition for preventing or ameliorating pain containing the above compound, the stereoisomer thereof or the pharmaceutically acceptable salt thereof as an active ingredient.

The compound represented by formula 1 of the present invention can be used as food additive. In that case, the compound can be added as it is or as mixed with other food components according to the conventional method. The mixing ratio of active ingredients can be regulated according to the purpose of use (prevention or alleviation). In general, the compound represented by formula 1 of the present invention can be added at 0.1 to 90 weight parts by the total food weight. However, if long term administration is required for health and hygiene or regulating health condition, the content can be lower than the above but higher content can be accepted as well since the compound has been proved to be very safe.

The composition for health beverages of the present invention can additionally include various flavors or natural carbohydrates, etc, like other beverages in addition to the compound. The natural carbohydrates above can be one of monosaccharides such as glucose and fructose; disaccharides such as maltose and sucrose; polysaccharides such as dextrin and cyclodextrin; and sugar alcohols such as xilytole, sorbitol and erythritol. Besides, natural sweetening agents (thaumatin, stevia extract, for example rebaudioside A, glycyrrhizin, etc.) and synthetic sweetening agents (saccharin, aspartame, etc.) can be included as a sweetening agent. The content of the natural carbohydrate is preferably 1-20 g and more preferably 5-12 g in 100 g of the composition of the present invention.

In addition to the ingredients mentioned above, the compound represented by formula 1 of the present invention can include in variety of nutrients, vitamins, minerals (electrolytes), flavors including natural flavors and synthetic flavors, coloring agents and extenders (cheese, chocolate, etc.), pectic acid and its salts, alginic acid and its salts, organic acid, protective colloidal viscosifiers, pH regulators, stabilizers, antiseptics, glycerin, alcohols, carbonators which used to be added to soda, etc. The compound represented by formula 1 of the present invention can also include natural fruit juice, fruit beverages and fruit flesh addable to vegetable beverages.

In another aspect of the present invention, the present invention provides a method for treating pain comprising a step of administering the above compound to a subject in need thereof. In another aspect of the present invention, the present invention provides the above compound for use in the prevention or treatment of pain. In another aspect of the present invention, the present invention provides a use of the above compound for preparing a medicament for use in the prevention or treatment of pain.

In another aspect of the present invention, the present invention provides a pharmaceutical kit for preventing or treating pain comprising the first component containing the above compound, the stereoisomer thereof or the pharmaceutically acceptable salt thereof as an active ingredient; and the second component containing an analgesic as an active ingredient.

At this time, the analgesic can be used without limitation, if it is a known one. The analgesic can be an anti-inflammatory analgesic (NSAID such as a COX inhibitor) or an opioid-based analgesic. Some specific examples of the analgesic include acetaminophen, aspirin, ibuprofen, ketoprofen, meloxicam, diclofenac potassium, etodolac, sulindac, indomethacin, celecoxib, valdecoxib, rofecoxib, celecoxib, hydrocodone, oxymorphone, buprenorphine, fentanyl, hydromorphone, tramadol or combinations thereof.

The compound provided in one aspect of the present invention has excellent TrkA inhibitory activity and exhibits excellent pain inhibitory effects in an animal model of pain after a surgery, and thus can be effectively used as an analgesic. This is supported by examples and experimental examples described hereinafter.

Hereinafter, the present invention will be described in detail by the following examples and experimental examples.

However, the following examples and experimental examples are only for illustrating the present invention, and the contents of the present invention are not limited thereto.

<Example 1> N-(3-chlorophenyl)-5-(pyridine-3-yl)-1H-pyrazolo[3,4-c]pyridine-3-amine

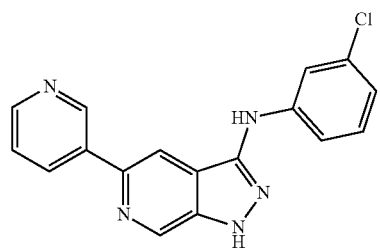 [SMILES: Clc1cccc(Nc2n[nH]c3cnc(-c4cccnc4)cc23)c1]

The compound of example 1 was prepared with reference to Korean Patent No. 10-1753652.

<Example 2> N-(3,4-dichlorophenyl)-5-(1-(piperidine-4-yl)-1H-pyrazole-4-yl)-1H-pyrazolo[3,4-c]pyridine-3-amine

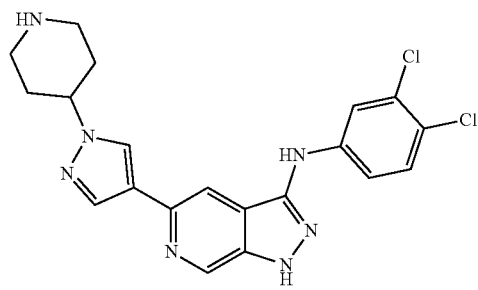 [SMILES: Clc1ccc(Nc2n[nH]c3cnc(-c4cnn(C5CCNCC5)c4)cc23)cc1Cl]

The compound of example 2 was prepared with reference to Korean Patent No. 10-1753652.

<Example 3> N-(3,5-dichlorophenyl)-5-(1-(piperidine-4-yl)-1H-pyrazole-4-yl)-1H-pyrazolo[3,4-c]pyridine-3-amine

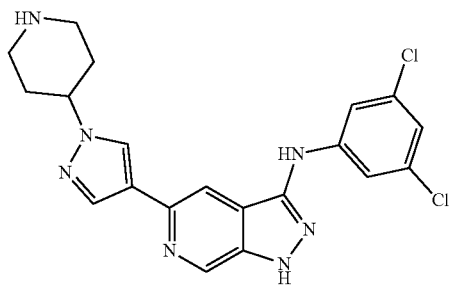 [SMILES: Clc1cc(Cl)cc(Nc2n[nH]c3cnc(-c4cnn(C5CCNCC5)c4)cc23)c1]

The compound of example 3 was prepared with reference to Korean Patent No. 10-1753652.

<Example 4> N-(3-chlorophenyl)-5-(1-methyl-1H-pyrazole-4-yl)-1H-pyrazolo[3,4-b]pyridine-3-amine

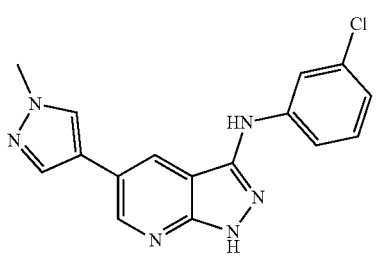 [SMILES: Cn1cc(-c2cnc3[nH]nc(Nc4cccc(Cl)c4)c3c2)cn1]

The compound of example 4 was prepared with reference to Korean Patent No. 10-1753652.

<Example 5> N-(3,4-dichlorophenyl)-5-(1-methyl-1H-pyrazole-4-yl)-1H-pyrazolo[3,4-b]pyridine-3-amine

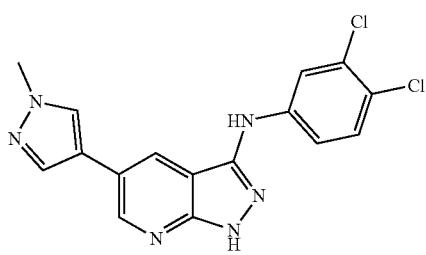 [SMILES: Cn1cc(-c2cnc3[nH]nc(Nc4ccc(Cl)c(Cl)c4)c3c2)cn1]

The compound of example 5 was prepared with reference to Korean Patent No. 10-1753652.

<Example 6> N-(3,5-dichlorophenyl)-5-(1-methyl-1H-pyrazole-4-yl)-1H-pyrazolo[3,4-b]pyridine-3-amine

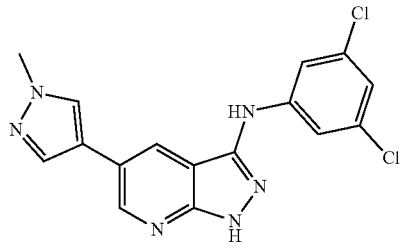 [SMILES: Cn1cc(-c2cnc3[nH]nc(Nc4cc(Cl)cc(Cl)c4)c3c2)cn1]

The compound of example 6 was prepared with reference to Korean Patent No. 10-1753652.

<Example 7> N-(3,5-dichlorophenyl)-5-(1-(piperidine-4-yl)-1H-pyrazole-4-yl)-1H-pyrazolo[3,4-b]pyridine-3-amine

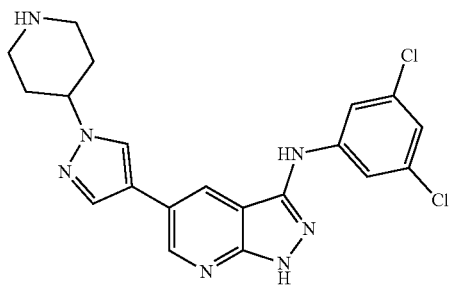 [SMILES: Clc1cc(Cl)cc(Nc2n[nH]c3ncc(-c4cnn(C5CCNCC5)c4)cc23)c1]

The compound of example 7 was prepared with reference to Korean Patent No. 10-1753652.

<Example 8> 4-(4-methylpiperazine-1-yl)-N-(5-(1-(piperidine-4-yl)-1H-pyrazole-4-yl)-1H-pyrazolo[3,4-b]pyridine-3-yl)benzamide

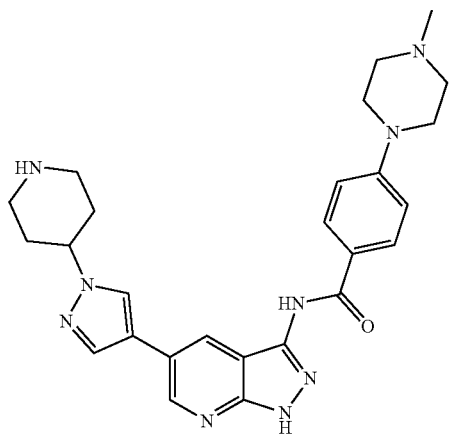 [SMILES: CN1CCN(c2ccc(C(=O)Nc3n[nH]c4ncc(-c5cnn(C6CCNCC6)c5)cc34)cc2)CC1]

The compound of example 8 was prepared with reference to Korean Patent No. 10-1753654.

<Example 9> N-(5-(3-(3-isopropylureido)phenyl)-1H-pyrazolo[3,4-b]pyridine-3-yl)-4-(4-methylpiperazine-1-yl)benzamide

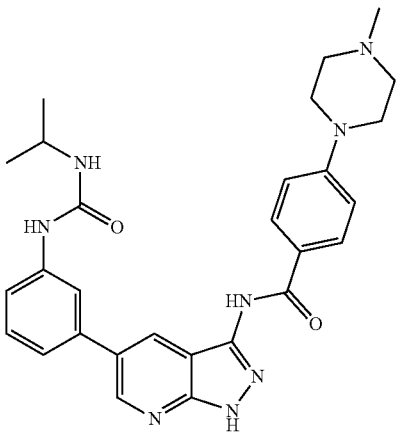 [SMILES: CC(C)NC(=O)Nc1cccc(-c2cnc3[nH]nc(NC(=O)c4ccc(N5CCN(C)CC5)cc4)c3c2)c1]

The compound of example 9 was prepared with reference to Korean Patent No. 10-1753654.

<Example 10> 4-(4-methylpiperazine-1-yl)-N-(5-phenyl-1H-pyrazolo[3,4-b]pyridine-3-yl)benzamide

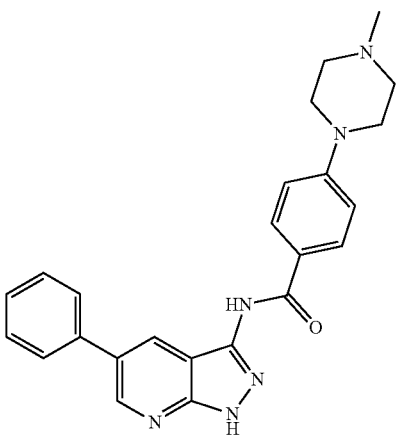 [SMILES: CN1CCN(c2ccc(C(=O)Nc3n[nH]c4ncc(-c5ccccc5)cc34)cc2)CC1]

The compound of example 10 was prepared with reference to Korean Patent No. 10-1753654.

<Example 11> N-(5-(4-fluorophenyl)-1H-pyrazolo[3,4-b]pyridine-3-yl)-4-(4-methylpiperazine-1-yl)benzamide

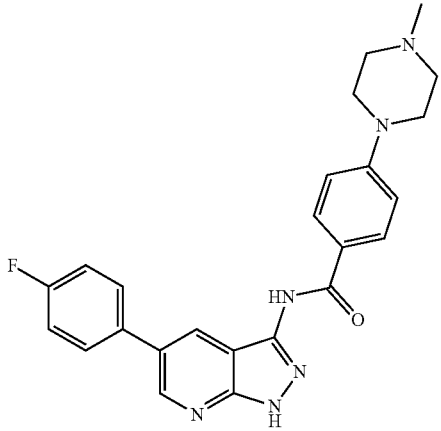 [SMILES: CN1CCN(c2ccc(C(=O)Nc3n[nH]c4ncc(-c5ccc(F)cc5)cc34)cc2)CC1]

The compound of example 11 was prepared with reference to Korean Patent No. 10-1753654.

<Example 12> 4-(2-methylpiperazine-1-yl)-N-(5-(pyridine-3-yl)-1H-pyrazolo[3,4-b]pyridine-3-yl)benzamide

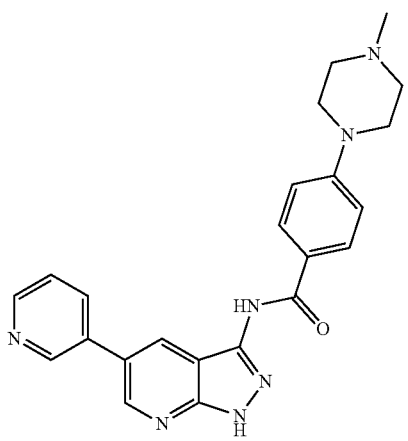

The compound of example 12 was prepared with reference to Korean Patent No. 10-1753654.

<Example 13> 4-(4-methylpiperazine-1-yl)-N-(5-(pyridine-4-yl)-1H-pyrazolo[3,4-b]pyridine-3-yl)benzamide

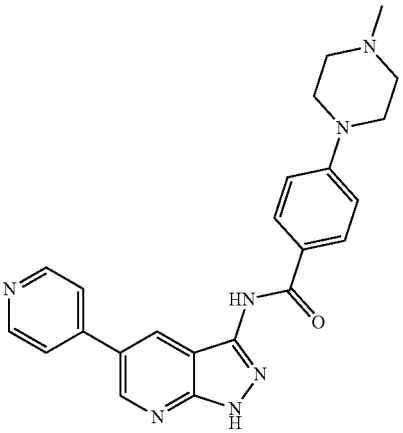 [SMILES: CN1CCN(c2ccc(C(=O)Nc3n[nH]c4ncc(-c5ccncc5)cc34)cc2)CC1]

The compound of example 13 was prepared with reference to Korean Patent No. 10-1753654.

<Example 14> N-(5-bromo-1H-pyrazolo[3,4-b]pyridine-3-yl)-4-(4-methylpiperazine-1-yl)benzamide

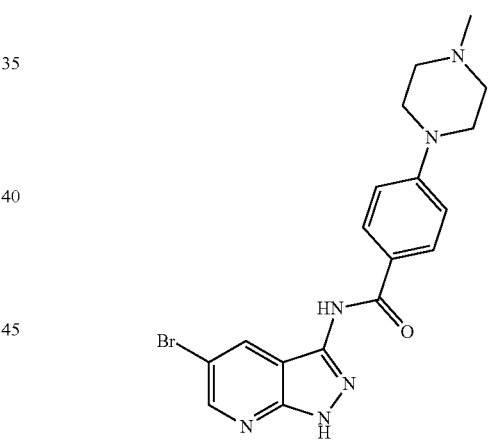

The compound of example 14 was prepared with reference to Korean Patent No. 10-1753654.

<Example 15> 2,6-dichloro-4-(4-(1-(piperidine-4-yl)-1H-pyrazole-4-yl)-7H-pyrrolo[2,3-d]pyrimidine-5-yl)phenol

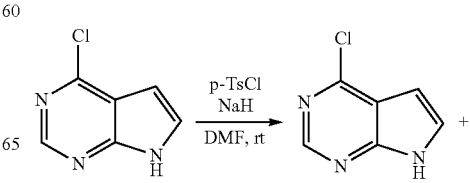

17
-continued

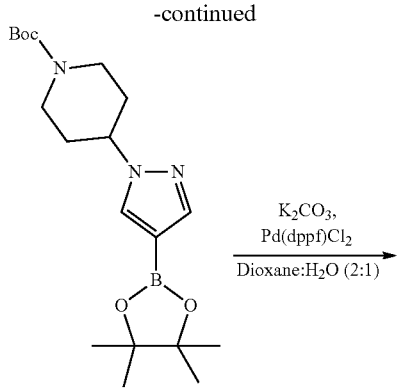

K₂CO₃,
Pd(dppf)Cl₂
―――――――→
Dioxane:H₂O (2:1)

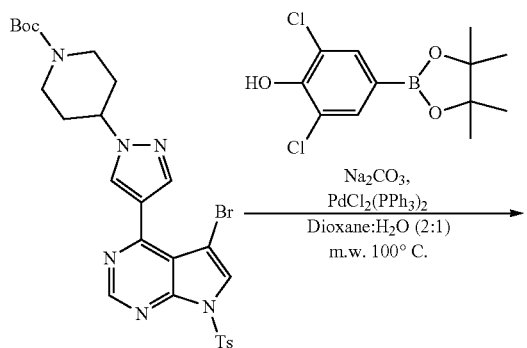

NBS
―――→
DMF, rt

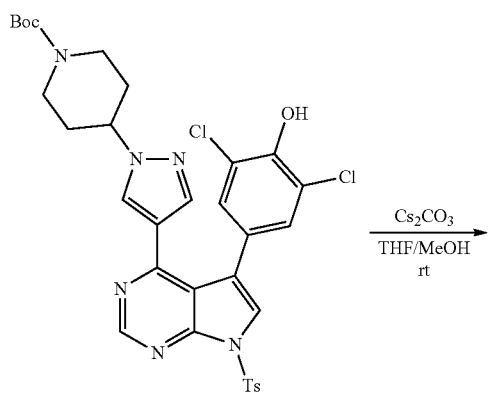

Na₂CO₃,
PdCl₂(PPh₃)₂
―――――――→
Dioxane:H₂O (2:1)
m.w. 100° C.

18
-continued

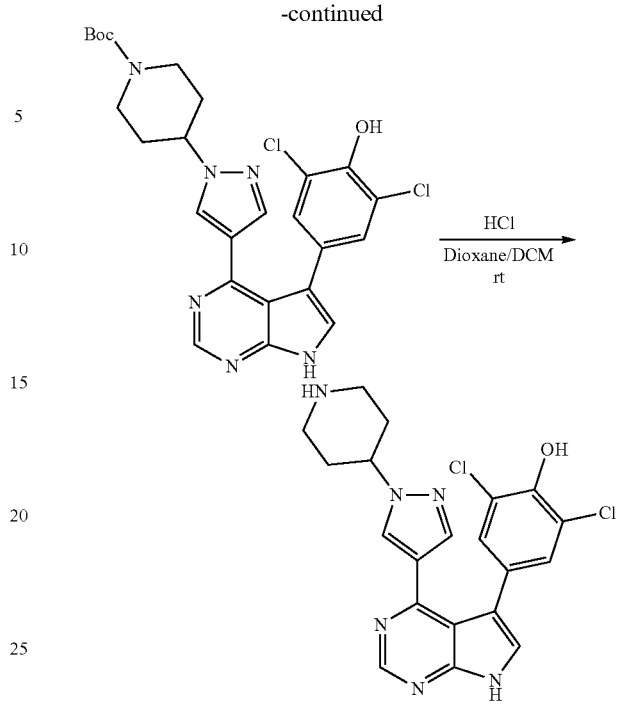

HCl
―――――――→
Dioxane/DCM
rt

Cs₂CO₃
―――→
THF/MeOH
rt

4-Chloro-7H-pyrrolo[2,3-d]pyrimidine (1.2 g, 7.84 mmol) was added to DMF (15 mL), and NaH (0.36 g, 9.00 mmol) was added thereto at 0° C. The mixture was stirred at room temperature for 20 minutes, and then p-toluenesulfonyl chloride (1.7 g, 8.91 mmol) was added thereto, followed by stirring at room temperature for 2 hours. Upon completion of the reaction, the solvent was removed under high pressure, dissolved in water, and extracted with dichloromethane (50 mL×3). The residue was purified by chromatography (ethyl acetate:hexane=2:3) to give 4-chloro-7-tosyl-7H-pyrrolo[2,3-d]pyrimidine (1.88 g, 78%).

¹H NMR (CDCl₃, 300 MHz): δ 8.77 (s, 1H), 8.01 (d, J=8.4 Hz, 2H), 7.79 (d, J=4.3 Hz, 1H), 7.32 (d, J=8.4 Hz, 2H), 6.71 (d, J=4.1 Hz, 1H), 2.40 (s, 3H).

4-chloro-7-tosyl-7H-pyrrolo[2,3-d]pyrimidine (1.0 g, 3.43 mmol), text-butyl 4-(4-(4,4,5,5-tetramethyl-1,3,2-dioxaborolan-2-yl)-1H-pyrazole-1-yl)piperidine-1-carboxylate (1.47 g, 3.89 mmol), potassium carbonate (1.35 g, 9.75 mmol) and Pd(dppf)Cl₂ (0.19 g, 0.26 mmol) were dissolved in a mixed solution of 1,4-dioxane and water (2:1), which was heated at 85° C. for 2 hours. Upon completion of the reaction, the solvent was removed under high pressure, dissolved in water, and extracted with ethyl acetate (50 mL×3). The residue was purified by chromatography to give tert-butyl 4-(4-(7-tosyl-7H-pyrrolo[2,3-d]pyrimidine-4-yl)-1H-pyrazole-1-yl)piperidine-1-carboxylate (1.24 g, 69%).

¹H NMR (CDCl₃, 300 MHz): δ 8.54 (s, 1H), 8.06 (d, J=7.8 Hz, 2H), 7.86 (d, J=1.9 Hz, 1H), 7.76 (s, 1H), 7.71 (d, J=3.9 Hz, 1H), 7.65 (s, 1H), 7.28 (s, 1H), 6.57 (d, J=4.0 Hz, 1H), 4.25-4.31 (m, 1H), 3.81-3.88 (m, 2H), 2.91 (t, J=12.6 Hz, 2H), 2.39 (s, 3H), 2.17 (d, J=10.5 Hz, 2H), 1.93-1.99 (m, 2H), 1.48 (s, 9H).

Tert-butyl 4-(4-(7-tosyl-7H-pyrrolo[2,3-d]pyrimidine-4-yl)-1H-pyrazole-1-yl)piperidine-1-carboxylate (1.4 g, 2.67 mmol) and N-bromosuccinimide (0.52 g, 2.93 mmol) were dissolved in DMF, followed by stirring at room temperature for 2 hours. Upon completion of the reaction, the solvent was removed under high pressure, dissolved in water, and extracted with ethyl acetate (50 mL×3). The residue was purified by chromatography to give tert-butyl 4-(4-(5-bromo-7-tosyl-7H-pyrrolo[2,3-d]pyrimidine-4-yl)-1H-pyrazole-1-yl)piperidine-1-carboxylate (1.53 g, 87%).

$^1$H NMR (CDCl$_3$, 300 MHz): δ 8.92 (s, 1H), 8.14 (d, J=4.2 Hz, 2H), 8.10 (s, 2H), 7.82 (d, J=4.2 Hz, 1H), 7.35 (d, J=8.4 Hz, 2H), 4.10-4.38 (m, 3H), 2.91 (t, J=12.1 Hz, 2H), 2.40 (s, 3H), 2.17-2.22 (m, 2H), 1.92-1.97 (m, 2H), 1.47 (s, 9H).

Tert-butyl 4-(4-(5-bromo-7-tosyl-7H-pyrrolo[2,3-d]pyrimidine-4-yl)-1H-pyrazole-1-yl)piperidine-1-carboxylate (0.24 g, 0.40 mmol), 2,6-dichloro-4-(4,4,5,5-tetramethyl-1,3,2-dioxaborolan-2-yl)phenol (139 mg, 0.48 mmol), sodium carbonate (127 mg, 1.20 mmol) and PdCl$_2$(PPh$_3$)$_2$ (6 mg, 0.008 mmol) were dissolved in a mixed solution of 1,4-dioxane and water (2:1), and heated at 100° C. under microwave condition for 20 minutes. Upon completion of the reaction, the solvent was removed under high pressure, dissolved in water, and extracted with ethyl acetate. The residue was purified by chromatography to give tert-butyl 4-(4-(5-(3,5-dichloro-4-hydroxyphenol)-7-tosyl-7H-pyrrolo[2,3-c]pyrimidine-4-yl)-1H-pyrazole-1-yl)piperidine-1-carboxylate (123 mg, 45%).

$^1$H NMR (DMSO-d$_6$, 300 MHz): δ 8.92 (s, 1H), 8.12 (d, J=4.2 Hz, 2H), 8.10 (d, J=1.5 Hz, 2H), 7.82 (s, 1H), 7.42 (s, 2H), 7.33 (d, J=8.0 Hz, 2H), 4.21-4.37 (m, 1H), 2.91 (t, J=12.5 Hz, 2H), 2.12-2.22 (m, 2H), 1.89-2.04 (m, 2H), 1.47 (s, 9H), 1.23-1.29 (m, 2H).

Tert-butyl 4-(4-(5-(3,5-dichloro-4-hydroxyphenol)-7-tosyl-7H-pyrrolo[2,3-d]pyrimidine-4-yl)-1H-pyrazole-1-yl)piperidine-1-carboxylate (137 mg, 0.20 mmol) was dissolved in tetrahydrofuran (2 mL) and methanol (1 mL), to which Cs$_2$CO$_3$ (228 mg, 0.70 mmol) was added, followed by stirring at room temperature for 30 minutes. Upon completion of the reaction, the solvent was removed under reduced pressure, dissolved in water, and extracted with ethyl acetate. The residue was purified by chromatography to give tert-butyl 4-(4-(5-(3,5-dichloro-4-hydroxyphenol)-7H-pyrrolo[2,3-d]pyrimidine-4-yl)-1H-pyrazole-1-yl)piperidine-1-carboxylate (45 mg, 42%).

$^1$H NMR (DMSO-d$_6$, 300 MHz): δ 12.09 (br s, 1H), 8.65 (s, 2H), 8.28 (s, 1H), 7.42 (s, 2H), 7.01 (s, 1H), 4.22-4.38 (m, 1H), 2.92 (t, J=12.5 Hz, 2H), 2.12-2.23 (m, 2H), 1.89-2.04 (m, 2H), 1.48 (s, 9H), 1.22-1.30 (m, 2H).

Tert-butyl 4-(4-(5-(3,5-dichloro-4-hydroxyphenol)-7H-pyrrolo[2,3-d]pyrimidine-4-yl)-1H-pyrazole-1-yl)piperidine-1-carboxylate (53 mg, 0.10 mmol) was dissolved in dichloromethane (3 mL), to which 4 M HCl (0.5 mL, 2.0 mmol) dissolved in 1,4-dioxane was added, followed by stirring at room temperature for 2 hours. The solvent was removed under reduced pressure, and the residue was purified by chromatography to give a target compound (36 mg, 85%).

$^1$H NMR (DMSO-d$_6$, 300 MHz): δ 12.14 (br s, 1H), 8.67 (s, 2H), 8.01 (s, 1H), 7.54 (s, 1H), 7.03 (s, 2H), 6.40 (s, 1H), 4.32-4.40 (m, 1H), 2.91 (t, J=12.5 Hz, 2H), 2.19-2.23 (m, 2H), 2.04 (d, J=12.5 Hz, 2H), 1.46-1.58 (m, 2H).

<Example 16> N-(7-(4-methoxybenzyl)-4-(1-(piperidine-4-yl)-1H-pyrazole-4-yl)-7H-pyrrolo[2,3-d]pyrimidine-5-yl)-4-(4-methylpiperazine-1-yl)benzamide

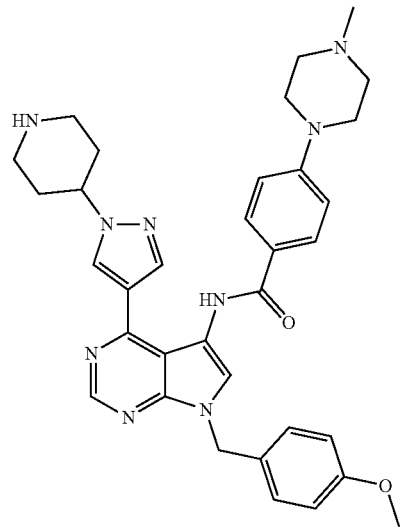 [SMILES: COc1ccc(Cn2cc(NC(=O)c3ccc(N4CCN(C)CC4)cc3)c3c(-c4cnn(C5CCNCC5)c4)ncnc32)cc1]

The compound of example 16 was prepared with reference to Korean Patent No. 10-1753654.

<Example 17> 4-(4-methylpiperazine-1-yl)-N-(4-(1-(piperidine-4-yl)-1H-pyrazole-4-yl)-7H-pyrrolo[2,3-d]pyrimidine-5-yl)benzamide

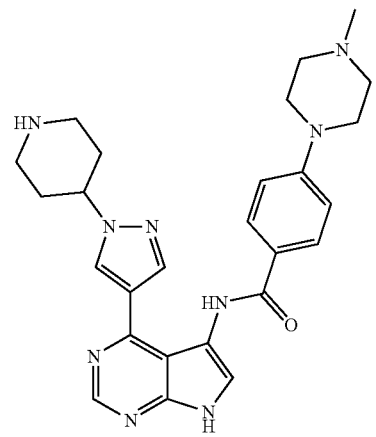 [SMILES: CN1CCN(c2ccc(C(=O)Nc3c[nH]c4ncnc(-c5cnn(C6CCNCC6)c5)c34)cc2)CC1]

The compound of example 17 was prepared with reference to Korean Patent No. 10-1753654.

<Example 18> tert-butyl 4-(4-(5-(4-(4-methylpiperazine-1-yl)benzamido)-7H-pyrrolo[2,3-d]pyrimidine-4-yl)-1H-pyrazole-1-yl)piperidine-1-carboxylate

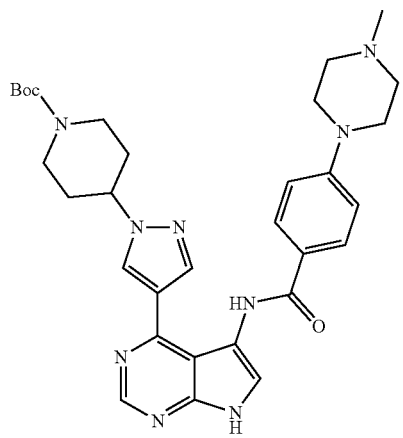 [SMILES: CN1CCN(c2ccc(C(=O)Nc3c[nH]c4ncnc(-c5cnn(C6CCN(C(=O)OC(C)(C)C)CC6)c5)c34)cc2)CC1]

The compound of example 18 was prepared with reference to Korean Patent No. 10-1753654.

<Example 19> 4-(4-methylpiperazine-1-yl)-N-(4-(4-(pyrrolidine-1-yl)piperidine-1-yl)-7H-pyrrolo[2,3-d]pyrimidine-5-yl)benzamide

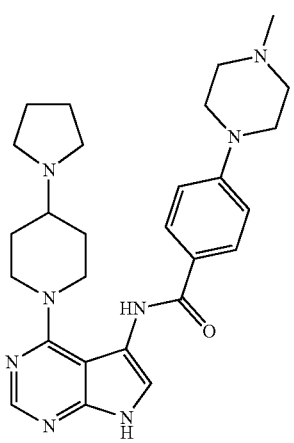 [SMILES: CN1CCN(c2ccc(C(=O)Nc3c[nH]c4ncnc(N5CCC(N6CCCC6)CC5)c34)cc2)CC1]

The compound of example 19 was prepared with reference to Korean Patent No. 10-1753654.

<Example 20> 1-(5-(4-(4-methylpiperazine-1-yl)benzamido)-7H-pyrrolo[2,3-d]pyrimidine-4-yl)piperidine-4-carboxamide

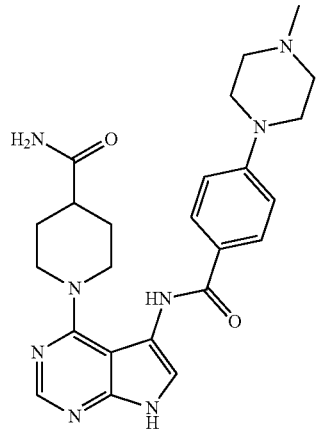 [SMILES: CN1CCN(c2ccc(C(=O)Nc3c[nH]c4ncnc(N5CCC(C(N)=O)CC5)c34)cc2)CC1]

The compound of example 20 was prepared with reference to Korean Patent No. 10-1753654.

<Example 21> 4-(4-methylpiperazine-1-yl)-N-(4-(3-ureidopiperidine-1-yl)-7H-pyrrolo[2,3-d]pyrimidine-5-yl)benzamide

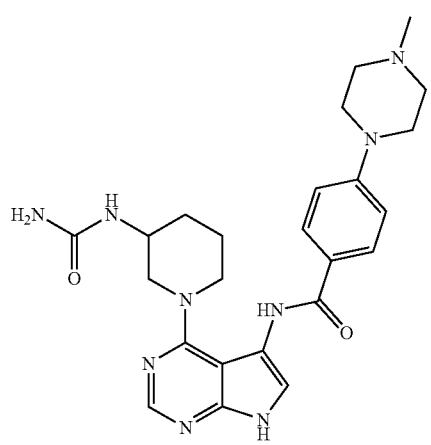 [SMILES: CN1CCN(c2ccc(C(=O)Nc3c[nH]c4ncnc(N5CCCC(NC(N)=O)C5)c34)cc2)CC1]

The compound of example 21 was prepared with reference to Korean Patent No. 10-1753654.

<Example 22> 4-fluoro-N-(5-(1-(piperidine-4-yl)-1H-pyrazolo-4-yl)-1H-pyrazolo[3,4-b]pyridine-3-yl)benzamide A. Preparation of tert-butyl 4-(4-(6-chloro-5-cyanopyridine-3-yl)-1H-pyrazole-1-yl)piperidine-1-carboxylate

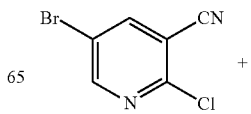

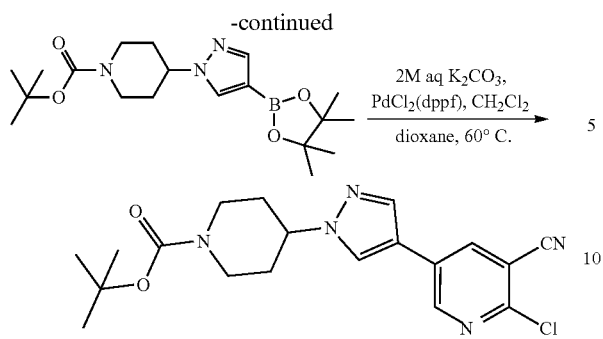

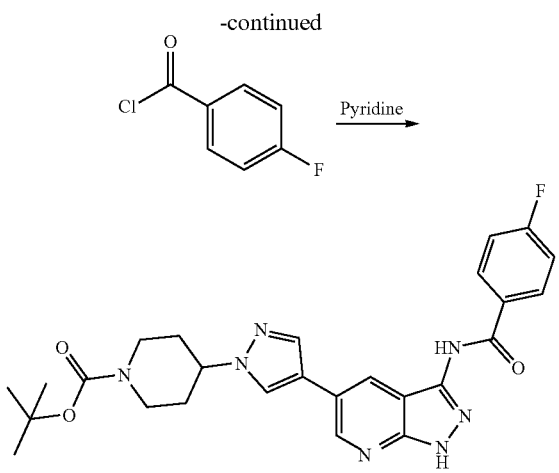

A mixture of 5-bromo-2-chloronicotinonitrile (100 mg, 0.460 mmol) dissolved in dioxane (20 mL), tert-butyl 4-(4-(4,4,5,5-tetramethyl-1,3,2-dioxaborolene-2-yl)-1H-pyrazole-1-yl)piperidine-1-carboxylate (174 mg, 0.460 mmol), $K_2CO_3$ (191 mg, 1.380 mmol), $PdCl_2(dppf)$ (68 mg, 0.046 mmol) and water (0.3 mL, 16.556 mmol) was treated with argon, and heat-treated at 90° C. for 8 hours in a sealed tube. The heat-treated solution was diluted with brine (100 mL) and extracted with ethyl acetate (3×50 mL). The organic layer was dried over anhydrous $Na_2SO_4$ and concentrated in vacuo. The product was purified by column chromatography to give tert-butyl 4-(4-(6-chloro-5-cyanopyridine-3-yl)-1H-pyrazole-1-yl)piperidine-1-carboxylate (150 mg, 84%).

B. Preparation of tert-butyl 4-(4-(3-amino-1H-pyrazolo[3,4-b]pyridine-5-yl)-1H-pyrazole-1-yl)piperidine-1-carboxylate

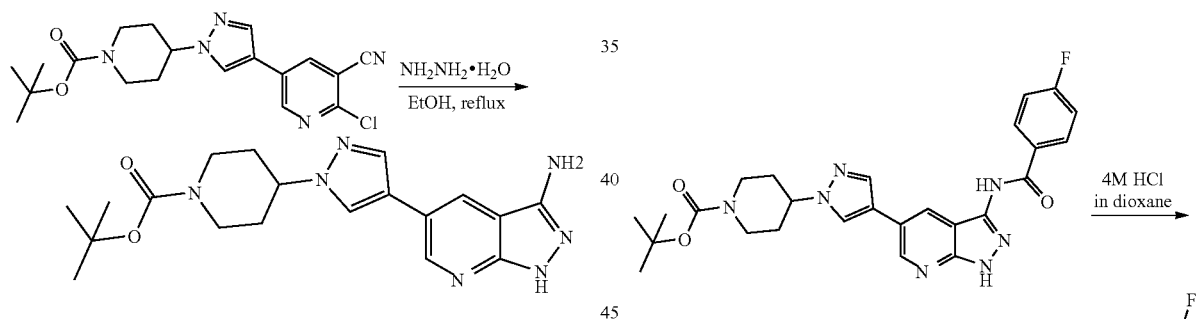

Hydrazine hydrate (98 mg, 1.934 mmol) was added to a stirred solution of tert-butyl 4-(4-(6-chloro-5-cyanopyridine-3-yl)-1H-pyrazole-1-yl)piperidine-1-carboxylate (150 mg, 0.387 mmol) dissolved in ethanol. The reaction mixture was refluxed for 6 hours, stirred and cooled, and the resulting solid was filtered and dried in vacuo to give tert-butyl 4-(4-(3-amino-1H-pyrazolo[3,4-b]pyridine-5-yl)-1H-pyrazole-1-yl)piperidine-1-carboxylate (140 mg, 94%).

C. Preparation of tert-butyl 4-(4-(3-(4-fluorobenzamido)-1H-pyrazolo[3,4-b]pyridine-5-yl)-1H-pyrazole-1-yl)piperidine-1-carboxylate

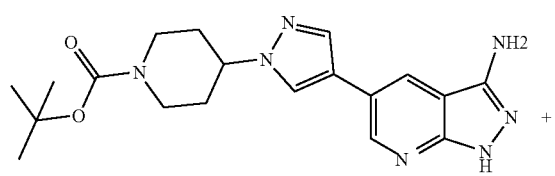

4-fluorobenzoyl chloride (44 μl, 0.365 mmol) was added to a solution of tert-butyl 4-(4-(3-amino-1H-pyrazolo[3,4-b]pyridine-5-yl)-1H-pyrazole-1-yl)piperidine-1-carboxylate (140 mg, 0.365 mmol) dissolved in pyridine (10 ml). The reaction mixture was stirred at room temperature for one day. The reaction mixture was concentrated and purified by column chromatography to give tert-butyl 4-(4-(3-(4-fluorobenzamido)-1H-pyrazolo[3,4-b]pyridine-5-yl)-1H-pyrazole-1-yl)piperidine-1-carboxylate (90 mg, 49%).

D. Preparation of 4-fluoro-N-(5-(1-(piperidine-4-yl)-1H-pyrazole-4-yl)-1H-pyrazolo[3,4-b]pyridine-3-yl)benzamide A solution of 4.0 M HCl dissolved in 1,4 dioxane (5 mL) was added to a mixed solution of tert-butyl 4-(4-(3-(4-fluorobenzamido)-1H-pyrazolo[3,4-b]pyridine-5-yl)-1H-pyrazole-1-yl)piperidine-1-carboxylate (90 mg, 0.178 mmol) dissolved in ethyl acetate (10 mL), followed by stirring for 12 hours. The reaction mixture was concentrated to minimize the volume, and the residue was collected through a filter to give a target compound (70 mg, 89%).

$^1$H NMR (400 MHz, DMSO-$d_6$): δ 11.08 (s, 1H), 9.34 (bs, 1H), 9.07 (bs, 1H), 8.87-8.82 (m, 1H), 8.41-8.31 (m, 2H), 8.22-8.14 (m, 2H), 8.01 (s, 1H), 7.39 (t, J=8.85 Hz, 2H), 4.58-4.46 (m, 1H), 3.36 (d, J=12.21 Hz, 2H), 3.07 (q, J=10.68 Hz, 2H), 2.30-2.12 (m, 4H).

<Example 23> 2,6-dichloro-4-(4-((1s,4s)-4-hydroxycyclohexylamino)-7H-pyrrolo[2,3-d]pyrimidine-5-yl)phenol

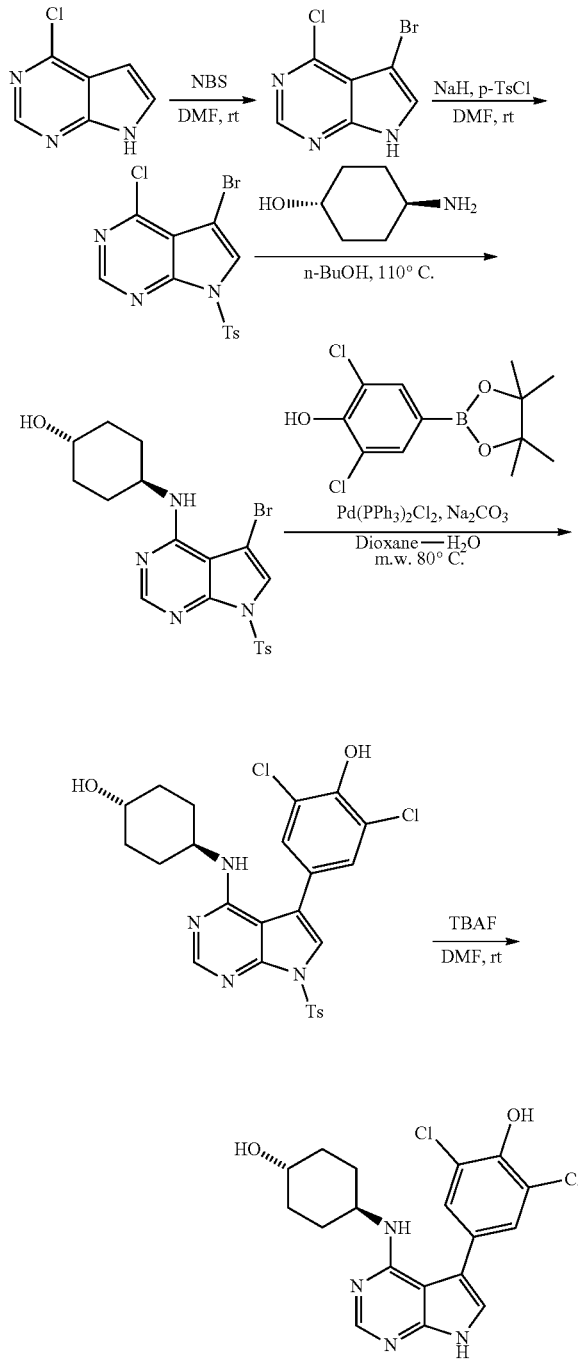

DMF (30 mL) was added to 4-chloro-7H-pyrrolo[2,3-d]pyrimidine (2 g, 13.02 mmol), to which NBS (2.52 g, 14.24 mmol) was added at 0° C. The mixture was stirred at room temperature for 3 hours. Upon completion of the reaction, the solvent was removed under high pressure, and the resultant was mixed with water, filtered, washed with hexane, and dried to give 5-bromo-4-chloro-7H-pyrrolo[2,3-d]pyrimidine (2.66 g, 88%).

$^1$H NMR (DMSO, 300 MHz): δ 7.81 (s, 1H), 8.76 (s, 1H), 5.02 (br s, 1H).

NaH (0.41 g, 10.3 mmol) was added to 5-bromo-4-chloro-7H-pyrrolo[2,3-d]pyrimidine (1.2 g, 5.16 mmol) dissolved in DMF (10 mL), followed by stirring at 0° C. for 30 minutes. P-tosyl chloride (1.36 g, 7.16 mmol) was added to the mixture, which was stirred at room temperature for 6 hours. Upon completion of the reaction, water was added thereto, followed by stirring for 10 minutes. The resultant was collected by filtration and dried to give 5-bromo-4-chloro-7-tosyl-7H-pyrrolo[2,3-d]pyrimidine (1.79 g, 90%).

$^1$H NMR (CDCl$_3$, 300 MHz): δ 8.76 (s, 1H), 8.09 (d, 2H, J=8.1 Hz), 7.54 (s, 1H), 7.34 (d, 2H, J=8.1 Hz), 2.41 (s, 3H).

N-BuOH (10 mL), trans-4-aminocyclohexane-1-ol (223 mg, 1.94 mmol) and DIPEA (2.58 mmol) were added to 5-bromo-4-chloro-7-tosyl-7H-pyrrolo[2,3-d]pyrimidine (500 mg, 1.29 mmol). The mixture was heated at 110° C. for 3 hours. The solvent was removed under high pressure and the residue was purified by chromatography to give (trans)-4-((5-bromo-7-tosyl-7H-pyrrolo[2,3-d]pyrimidine-4-yl)amino)cyclohexane-1-ol (540 mg, 90%).

$^1$H NMR (CDCl$_3$, 300 MHz): δ 8.37 (s, 1H), 8.06 (d, 2H, J=8.3 Hz), 7.45 (s, 1H), 7.31 (d, 2H, J=8.2 Hz), 5.87 (d, 1H), 4.12 (m, 1H), 3.70 (m, 1H), 2.40 (s, 3H), 2.16 (m, 2H), 2.03 (m, 2H), 1.54 (m, 2H), 1.31 (m, 2H).

(Trans)-4-((5-bromo-7-tosyl-7H-pyrrolo[2,3-d]pyrimidine-4-yl)amino)cyclohexane-1-ol (200 mg, 0.43 mmol), 2,6-dichloro-4-(4,4,5,5-tetramethyl-1,3,2-dioxaborolene-2-yl)phenol (0.86 mmol), Na$_2$CO$_3$ (0.86 mmol), dioxane (4 mL) and water (1 mL) were added into a microwave vial. The solvent was degassed for 15 minutes, to which Pd(PPh$_3$)$_2$Cl$_2$ (10 mol %) was added, followed by irradiating microwave at 80° C. for 30 minutes. The solution was filtered with a celite layer, and the filtrate was washed with brine (10 mL×5). The organic layer was concentrated by chromatography (10% methanol:dichloromethane) to give (trans)-2,6-dichloro-4-(4-((-4-hydroxycyclohexyl)amino)-7-tosyl-7H-pyrrolo[2,3-d]pyrimidine-5-yl) (40%).

$^1$H NMR (CDCl$_3$, 300 MHz): δ 8.46 (s, 1H), 8.11 (d, 2H, J=8.36 Hz), 7.41 (s, 1H), 7.36 (s, 2H), 7.31 (d, 2H, J=8.13 Hz), 6.03 (m, 1H), 4.71 (d, 1H), 4.09 (m, 1H), 3.63 (m, 1H), 2.41 (s, 3H), 2.05 (m, 2H), 1.89 (m, 2H), 1.40 (m, 2H), 1.10 (m, 2H).

1 M TBAF (in THF) was added to the intermediate (trans)-2,6-dichloro-4-(4-((-4-hydroxycyclohexyl)amino)-7-tosyl-7H-pyrrolo[2,3-d]pyrimidine-5-yl)phenol, followed by stirring at room temperature for 20 hours. The reactant was concentrated under reduced pressure and purified by chromatography (15% methanol:dichloromethane+0.1% ammonia water) to give a target compound (40%).

$^1$H NMR (DMSO-d$_6$, 300 MHz): δ 11.82 (br s, 1H), 10.16 (br s, 1H), 8.17 (s, 1H), 7.42 (s, 2H), 7.29 (s, 1H), 5.27 (d, 1H), 4.54 (m, 1H), 4.01 (m, 1H), 3.43 (m, 1H), 1.95 (m, 2H), 1.76 (m, 2H), 1.40 (m, 2H), 1.20 (m, 4H).

<Example 24> N-(4-(3,5-dichloro-4-hydroxyphenyl)-7H-pyrrolo[2,3-d]pyrimidine-5-yl)-4-(4-methylpiperazine-1-yl)benzamide
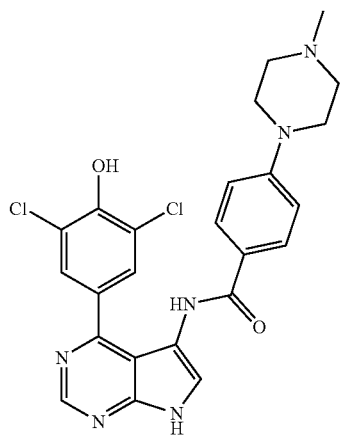 [SMILES: CN1CCN(c2ccc(C(=O)Nc3c[nH]c4ncnc(-c5cc(Cl)c(O)c(Cl)c5)c34)cc2)CC1]
The compound of example 24 was prepared with reference to Korean Patent No. 10-1753654.
The structures of the compounds prepared in examples 1 to 24 are shown in table 1 below.

TABLE 1-continued
| Example | Structure |
|---|---|
| 9 | 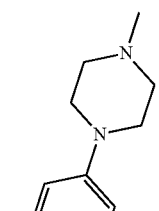 |
| 10 | 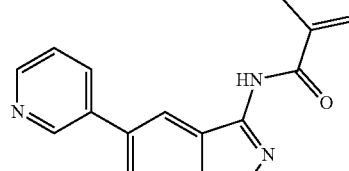 |
| 11 | 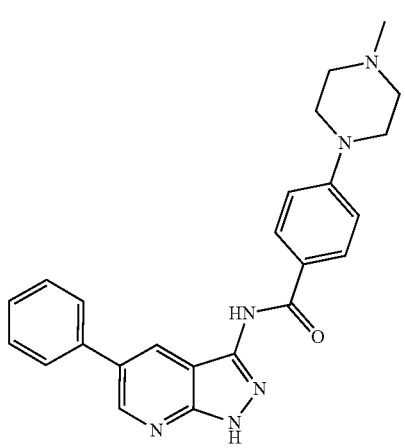 [SMILES: CN1CCN(c2ccc(C(=O)Nc3n[nH]c4ncc(-c5ccccc5)cc34)cc2)CC1] |
| 12 | 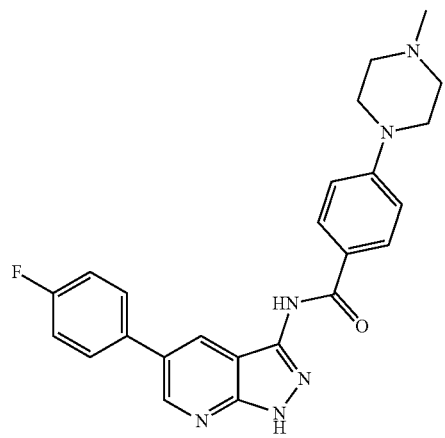 [SMILES: CN1CCN(c2ccc(C(=O)Nc3n[nH]c4ncc(-c5ccc(F)cc5)cc34)cc2)CC1] |
| 13 | |
| 14 | |

TABLE 1-continued
| Example | Structure |
|---------|-----------|
| 15 | 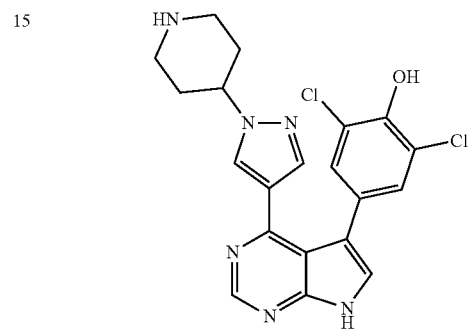 |
| 16 | 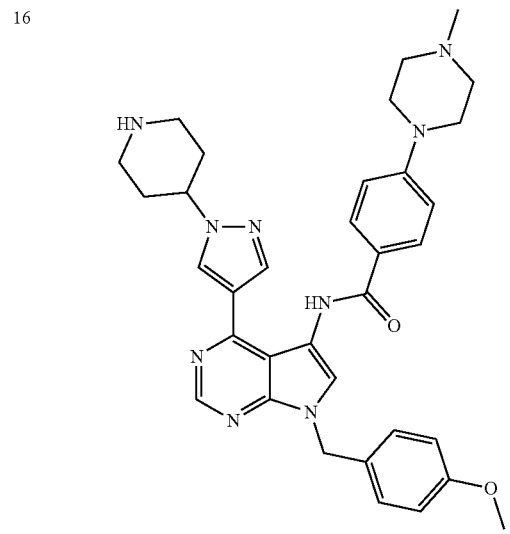 |
| 17 | 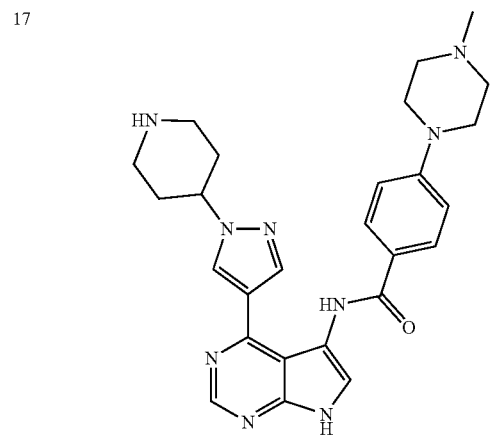 |
| 18 | 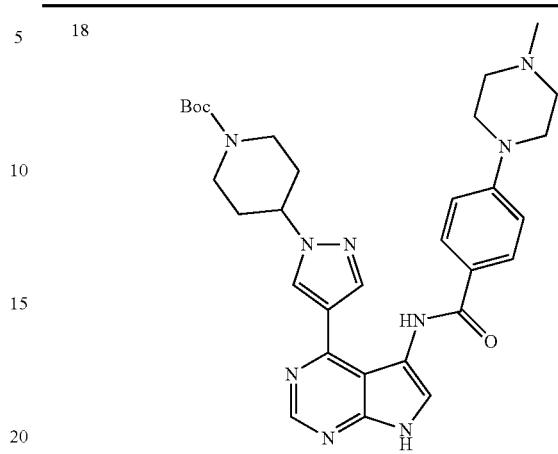 |
| 19 | 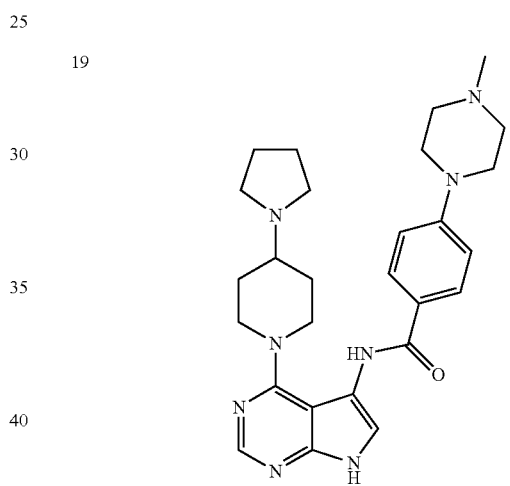 |
| 20 | 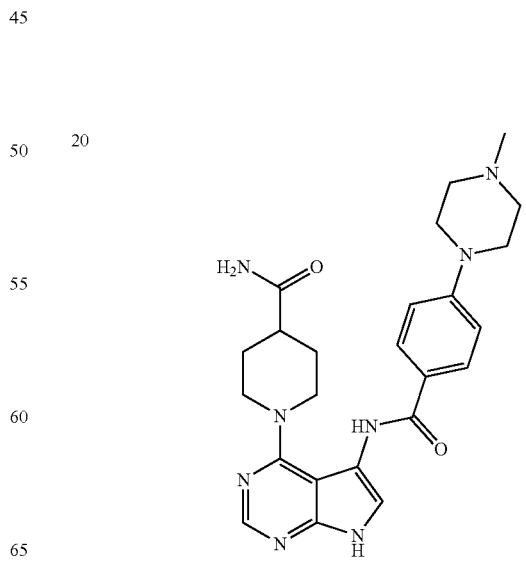 |

TABLE 1-continued

| Example | Structure |
|---|---|
| 21 | 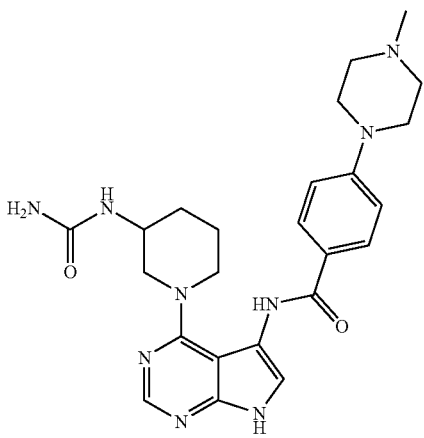 [SMILES: CN1CCN(c2ccc(C(=O)Nc3c[nH]c4ncnc(N5CCCC(NC(N)=O)C5)c34)cc2)CC1] |
| 22 | 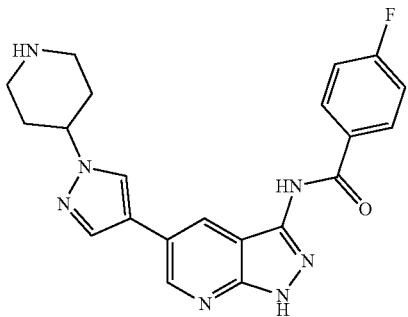 [SMILES: O=C(Nc1n[nH]c2ncc(-c3cnn(C4CCNCC4)c3)cc12)c1ccc(F)cc1] |
| 23 | 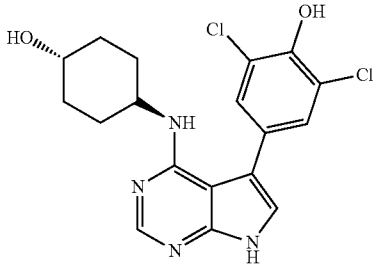 |
| 24 | 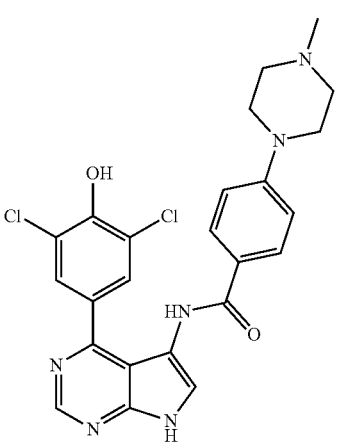 [SMILES: CN1CCN(c2ccc(C(=O)Nc3c[nH]c4ncnc(-c5cc(Cl)c(O)c(Cl)c5)c34)cc2)CC1] |

<Experimental Example 1> Evaluation of TrkA Inhibitory Activity

The TrkA inhibitory activity of the compounds was evaluated using CycLex® TrkA kinase assay/inhibitor screening kit of MBL International (Cat No. CY-1091). The test was carried out according to the analysis method provided by the manufacturer. The test method is as follows.

1. 1× wash buffer was prepared by diluting 10× wash buffer in ddH$_2$O.

2. 20×ATP solution (1.25 mM) was prepared by adding 1.6 mL of distilled water to the tube containing ATP dissolved in NA$_2$ salt and freeze-dried.

3. Kinase reaction buffer (ATP plus) was prepared using the 20×ATP solution as shown in table below.

TABLE 2

| Kinase reaction buffer (ATP plus) | 192 assay (2 plates) |
|---|---|
| Kinase buffer | 19 ml |
| 20× ATP solution | 1 ml |
| Total | 20 ml |

4. A working solution mixture and a solution of the appropriate concentration of the example compound to evaluate the activity of the example compound were prepared and dispensed into a 96-well plate as shown in table below.

TABLE 3

| Assay reagent | Test sample | Solvent control (DMSO) | Inhibitor control |
|---|---|---|---|
| Kinase reaction buffer (ATP plus) | 80 µl | 80 µl | 80 µl |
| 10× Test sample/inhibitor | 10 µl | — | — |
| Solvent for inhibitor 10× inhibitor (Positive control) | — | 10 µl | — |
| | — | — | 10 µl |
| TrkA Positive control (0.1 unit/µl) | 10 µl | 10 µl | 10 µl |

5. After dispensing the solutions into a 96-well plate, the plate was incubated at 30° C. for 30 minutes.

6. After incubation of the plate at 30° C. for 30 minutes, 200 µL of 1× wash buffer was added into each well of the plate, followed by washing. This process was repeated 5 times.

7. After washing the plate, 100 µL of HRP conjugated detection antibody (PX-39) was added into each well of the plate, followed by reaction at room temperature for 60 minutes.

8. Upon completion of the reaction, 200 µL of 1× wash buffer was added into each well of the plate, followed by washing. This process was repeated 5 times.

9. After washing the plate, 100 µL of substrate reagent containing chromogenic substrate and tetra-methylbenzidine (TMB) was added into each well of the plate, followed by incubation at room temperature for 5-15 minutes.

10. Upon completion of the reaction, 100 µL of stop solution (1 N H$_2$SO$_4$) was added into each well of the plate, followed by measuring OD$_{450}$ within 30 minutes.

The results are shown in table 4.

TABLE 4

| Example | % inhibition rate (based on 1 µM) | IC$_{50}$ (nM) |
|---|---|---|
| 1 | 12 | — |
| 2 | 6 | — |

TABLE 4-continued

| Example | % inhibition rate (based on 1 µM) | IC$_{50}$ (nM) |
|---|---|---|
| 3 | 6 | — |
| 4 | 59 | — |
| 5 | 32 | — |
| 6 | 32 | — |
| 7 | 37 | — |
| 8 | 99 | — |
| 9 | 81 | — |
| 10 | 98 | 212.6 |
| 11 | 99 | 218.5 |
| 12 | 98 | 308.5 |
| 13 | 99 | 179.2 |
| 14 | 101 | 121.7 |
| 15 | 95 | — |
| 16 | 8 | — |
| 17 | −11 | — |
| 18 | 24 | — |
| 19 | −1 | — |
| 20 | 4 | — |
| 21 | 0 | — |
| 22 | 99 | 436.1 |
| 23 | 100 | 57.9 |
| 24 | 49 | — |

—: NT (Not Tested)

<Experimental Example 2> Evaluation of Inhibitory Activity Against TrkB and TrkC The inhibitory activity of the example compounds against TrkB and TrkC was evaluated using PathHunter® eXpress TrkB or TrkC functional assay kit (Product Code: 93-0463E3 and 93-0464E3) of DiscoverX. The test was carried out according to the analysis method provided by the manufacturer. The test was carried out as follows over 2 or 3 days depending on the conditions of cells.

Day 1: Seeding of Cells

1. Before starting the experiment, the cell plating (CP) reagent stored at −80° C. was dissolved in a 37° C. water bath.
2. When the CP reagent was dissolved, cell vials for TrkB or TrkC were prepared to be dissolved.
3. Two U2OS cell vials (TrkB kit & TrkC kit) stored in liquid nitrogen were thawed.
4. 500 µL of CP reagent was added to the thawed cell vial, and the cells were sufficiently mixed by pipetting and transferred to a Conical tube in which 11.5 mL of CP reagent was dispensed.
5. 12 mL cells (1×10$^6$ cells in CP reagent) were seeded on a 96-well tissue culture treated plate (100 µL/well), followed by culture in a 37° C., 5% CO$_2$ humidified incubator for 24 hours or 48 hours.

Day 2 or Day 3: Treatment of Test Material

1. Test material, agonist and antagonist were prepared as stock solutions according to the experiment design.
   Test material: 10 mM Stock solution in DMSO
   Antagonist (GNF-5837): 10 mM Stock solution in 1.8674 mL DMSO
   Agonist: TrkB agonist→BDNF, TrkC agonist→NT-3
2. 10 mM stock solutions of teat material and antagonist having the concentration of 22 times more concentrated than the final screening concentration were prepared according to the experiment design.
3. Each well of the 96-well culture plate containing cells was treated with 5 µL of the solutions of teat material and antagonist having the concentration of 22 times more concentrated than the final screening concentration (#2), followed by incubation at 37° C. for 60 minutes.
4. During the incubation, 10 µg/mL stock solution of each agonist for TrkB and TrkC was prepared using a reconstitution buffer for the purpose of the experiment, and each well of the plate was treated with 5 µL of the prepared solution, followed by incubation at 19-25° C. for 3 hours.
5. During the incubation, a detection reagent working solution (4.75 ml Cell assay buffer, 1.25 ml Substrate Reagent 1, 0.25 ml Substrate Reagent 2) was prepared. Upon completion of the incubation, 55 µL of the working solution was added into each well of the plate.
7. The plate was incubated at room temperature for 60 minutes in a dark place, and the absorbance was measured with a luminescence plate reader.

The results are shown in table 5.

TABLE 5

| | TrkB | | TrkC | |
|---|---|---|---|---|
| Example | % inhibition rate (based on 1 µM) | IC$_{50}$ (nM) | % inhibition rate (based on 1 µM) | IC$_{50}$ (nM) |
| 1 | — | — | — | — |
| 2 | — | — | — | — |
| 3 | — | — | — | — |
| 4 | — | — | — | — |
| 5 | — | — | — | — |
| 6 | — | — | — | — |
| 7 | — | — | — | — |
| 8 | — | — | — | — |
| 9 | 1 | — | −20 | — |
| 10 | 27 | — | 49 | 1073.2 |
| 11 | 17 | — | 9 | — |
| 12 | 0 | — | −15 | — |
| 13 | −1 | — | 0 | — |
| 14 | −8 | — | −20 | — |
| 15 | 4 | — | −16 | — |
| 16 | — | — | — | — |
| 17 | — | — | — | — |
| 18 | — | — | — | — |
| 19 | — | — | — | — |
| 20 | — | — | — | — |
| 21 | — | — | — | — |
| 22 | −2 | — | 20 | — |
| 23 | 56 | 894.4 | 15 | — |
| 24 | — | — | — | — |

—: NT (Not Tested)

<Experimental Example 3> Evaluation of Pharmacological Activity in Postoperative Pain Model Sprague-Dawley male rats weighing around 150 g (Orient bio., Korea) were used. Rats were raised in an environment where a 12-hour light-dark cycle was maintained, 4 per transparent plastic cage covered with scob as bedding. Food and water were provided freely. To verify the analgesic effect of the example compounds, all rats were anesthetized with O$_2$ delivered from the induction chamber at a ratio of 3:3 of isoflurane and operated. Anesthetized rats were placed on a 37° C. warm plate to prevent hypothermia during the operation. The ipsilateral sole (left) of the hind paw of the experimental animal was disinfected with 10% povidone-iodine solution, and incised to a length of 1 cm with a #11 surgical knife. The incision was made starting from 0.5 cm of the proximal edge of the heel through the skin and fascia on the side of the ipsilateral sole toward the toe. After the incision, a gentle pressure was applied to the incision site to stop the bleeding and the skin was sutured. The surgical site was sterilized with 10% povidone-iodine solution, and gentamicin (8 mg/kg) was administered intraperitoneally to prevent infection. The analgesic effect of the compound on postoperative pain was evaluated in the experimental animals 2 days after the surgery. The evaluation was performed by Dixon's up-down method, a method of measuring mechanical allodynia using von-Frey filament, to calculate the withdraw threshold such as Chaplan suggested by Dixon. The formula for calculating the 50% withdrawal threshold (g) is as follows.

50% Withdrawal threshold (g)= $(10^{(x+kd)})/10^4$ [Mathematical Formula 1]

x=the value of the last tested filament (log unit value).
k=the value indicating positive/negative reaction by up-down method.
d=the value fixed at 0.224 as the average difference between stimuli.

The results are shown table 6 and FIGS. 1 to 10.

Table 6 shows the comparison result of the ED50 value of each compound and the ED50 value of the control drug in the postoperative pain animal model.

FIGS. 1 to 6 are graphs showing the optimal drug expression time of the compounds of Examples 10, 11, 12, 13, 14 and 15 in each postoperative pain animal model.

FIGS. 7 to 10 are graphs showing the pain suppressing effect of the compounds of Examples 10, 13, 14 and 15 according to the concentration at the optimal drug expression time in each postoperative pain animal model.

TABLE 6

|  | Route of drug administration | Maximum duration of drug efficacy (hr) | ED50 (mg/kg) |
| --- | --- | --- | --- |
| Example 10 | Oral | 0.5 | 3.8 |
| Example 13 | Oral | 1.0 | 11.5 |
| Example 14 | Oral | 0.5 | 3.8 |
| Example 15 | Oral | 0.5 | 20.1 |
| Lyrica (Pregabalin) | Oral | 1.0 | 17.5 |

<Manufacturing Example 1> Preparation of Pharmaceutical Preparations 1-1. Preparation of Powders

| Compound represented by formula 1 | 500 mg |
| --- | --- |
| Lactose | 100 mg |
| Talc | 10 mg |

Powders were prepared by mixing all the above components, which were filled in airtight packs according to the conventional method for preparing powders.

1-2. Preparation of Tablets

| Compound represented by formula 1 | 500 mg |
| --- | --- |
| Corn starch | 100 mg |
| Lactose | 100 mg |
| Magnesium stearate | 2 mg |

Tablets were prepared by mixing all the above components by the conventional method for preparing tablets.

1-3. Preparation of Capsules

| Compound represented by formula 1 | 500 mg |
| --- | --- |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

1-4. Preparation of Injectable Solutions

| Compound represented by formula 1 | 500 mg |
| --- | --- |
| Sterile distilled water for injection | proper amount |
| pH regulator | proper amount |

Injectable solutions were prepared by mixing all the above components, putting the mixture into 2 ml ampoules and sterilizing thereof by the conventional method for preparing injectable solutions.

1-5. Preparation of Liquid Formulations

| Compound represented by formula 1 | 100 mg |
| --- | --- |
| Isomerized sugar | 10 g |
| Mannitol | 5 g |
| Purified water | proper amount |

All the above components were dissolved in purified water. After adding lemon flavor, total volume was adjusted to be 100 ml by adding purified water. Liquid formulations were prepared by putting the mixture into brown bottles and sterilizing thereof by the conventional method for preparing liquid formulations.

INDUSTRIAL APPLICABILITY

The compound provided in one aspect of the present invention has excellent TrkA inhibitory activity and exhibits excellent pain inhibitory effects in a postoperative pain animal model, and thus can be effectively used as an analgesic.

What is claimed is:
1. A compound, a stereoisomer thereof or a pharmaceutically acceptable salt thereof, wherein the compound is any one compound selected from the group consisting of the following compounds:
   (14) N-(5-bromo-1H-pyrazolo[3,4-b]pyridine-3-yl)-4-(4-methylpiperazine-1-yl)benzamide;
   (15) 2,6-dichloro-4-(4-(1-(piperidine-4-yl)-1H-pyrazole-4-yl)-7H-pyrrolo[2,3-d]pyrimidine-5-yl)phenol;
   (22) 4-fluoro-N-(5-(1-(piperidine-4-yl)-1H-pyrazole-4-yl)-1H-pyrazolo[3,4-b]pyridine-3-yl)benzamide; and
   (23) 2,6-dichloro-4-(4-((1s,4s)-4-hydroxycyclohexylamino)-7H-pyrrolo[2,3-d]pyrimidine-5-yl)phenol.
2. A pharmaceutical composition for use treating pain containing the compound of claim 1, the stereoisomer thereof or the pharmaceutically acceptable salt thereof as an active ingredient.
3. The pharmaceutical composition for use according to claim 2, wherein the compound exhibits an activity of treating pain by inhibiting tropomyosin receptor kinase A (TrkA).
4. A health functional food composition for use in ameliorating pain containing the compound of claim 1, the stereoisomer thereof or the pharmaceutically acceptable salt thereof as an active ingredient.

5. A pharmaceutical kit for use in treating pain comprising a first component containing the compound of claim 1, the stereoisomer thereof or the pharmaceutically acceptable salt thereof as an active ingredient; and a second component containing an analgesic as an active ingredient.

6. A method for treating pain comprising a step of administering a compound, a stereoisomer thereof or a pharmaceutically acceptable salt thereof, wherein the compound is any one compound selected from the group consisting of the following compounds:
- (14) N-(5-bromo-1H-pyrazolo[3,4-b]pyridine-3-yl)-4-(4-methylpiperazine-1-yl)benzamide;
- (15) 2,6-dichloro-4-(4-(1-(piperidine-4-yl)-1H-pyrazole-4-yl)-7H-pyrrolo[2,3-d]pyrimidine-5-yl)phenol;
- (22) 4-fluoro-N-(5-(1-(piperidine-4-yl)-1H-pyrazole-4-yl)-1H-pyrazolo[3,4-b]pyridine-3-yl)benzamide; and
- (23) 2,6-dichloro-4-(4-((1s,4s)-4-hydroxycyclohexylamino)-7H-pyrrolo[2,3-d]pyrimidine-5-yl)phenol.

7. The method for treating pain according to claim 6, wherein the compound exhibits an activity of treating pain by inhibiting TrkA (tropomyosin receptor kinase A).

* * * * *